US006316433B1

(12) United States Patent
Rose et al.

(10) Patent No.: US 6,316,433 B1
(45) Date of Patent: Nov. 13, 2001

(54) METHOD FOR TREATMENT OF BACTERIAL INFECTIONS WITH ONCE OR TWICE-WEEKLY ADMINISTERED RIFALAZIL

(75) Inventors: Lynn M. Rose; David J. Porubek, both of Seattle; Alan B. Montgomery, Bellevue, all of WA (US)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/464,353

(22) Filed: Dec. 15, 1999

Related U.S. Application Data
(60) Provisional application No. 60/112,921, filed on Dec. 18, 1998.

(51) Int. Cl.[7] .......................... A61K 31/33; A61K 31/70
(52) U.S. Cl. ............................ 514/183; 514/30; 514/924
(58) Field of Search .................... 514/183, 30, 924

(56) References Cited

U.S. PATENT DOCUMENTS

| 4,983,602 | 1/1991 | Takehiko et al. | 514/229 |
| 5,786,349 | 7/1998 | Katsuji et al. | 514/183 |

FOREIGN PATENT DOCUMENTS

| 9602464 | 8/1996 | (JP) | 31/535 |

OTHER PUBLICATIONS

Klemens et al., "Activity of KRM–1648 in combination with isoniazide aganist Mycobacterium tuberulosis in murine model", Antimicrob. Agents Chemother. (1996), 40(2), 298–301 (abstract).*
Bermudez et al., "Activity of KRM–1648 alone or in combination with ethambutol or clarithromycin aganist Mycobacterium avium in beige mouse model of disseminated infection", Antimicrob. Agents Chemothe (1994), 38(8), 1844–1848.*
Norio Doi, Therapeutic Efficacy of Benzoxazinorifamycin KRM–1648 Against Experimental Murine Tuberculosis: A Study on the Efficacy of Short Course Treatment with the Intratracheal and Intravenous Infection Models, *Kekkaku*, 73:2, 53–64 (1998).
Kazunori Hosoe, et al., Pharmacokinetics of KRM–1648, A New Benzoxazinorifamycin, in Rats and Dogs, *Antimicrobial Agents and Chemotherapy*, 40:12, pp. 2749–2755 (Dec. 1996).

Brian P. Kelly, et al., Low–Dose Aerosol Infection Model for Testing Drugs for Efficacy Against *Mycobacterium tuberculosis*, *Antimicrobial Agents and Chemotherapy*, 40:12, pp. 2809–2812 (Dec. 1996).
H. Saito, et al., Therapeutic Effect of KRM–1648 With Various Antimicrobials Against *Mycobacterium avium* Complex Infection in Mice, *Tubercle and Lung Disease*, 76:51–58 (1995).
Masako Emori, et al., Evaluation of *In Vivo* Therapeutic Efficacy of a New Benzoxazinorifamycin , KRM–1648, in SCID Mouse Model for Disseminated *Mycobacterium avium* Complex Infection, *International Journal of Antimicrobial Agents* , 10:59–65, (1998).
Haruaki Tomioka, et al., *In Vitro* and *In Vivo* Antimycobacterial Activities of KRM–1648, a New Benzoxazinorifamycin, *Recent Res. Devel. In Antimicrob. Agents & Chemother.*, 2:37–68, (1997).
Tetsuo Hirata, et al., *In Vitro* and *In Vivo*Activities of the Benzoxazinorifamycin KRM–1648 Against *Mycobacterium tuberculosis*, *Antimicrobial Agents and Chemotherapy*, 39:10, pp. 2295–2303, (Oct. 1995).
Animal Models Murine Model with Low–Dose Aerosol Infection Useful, *Tuberculosis & Airborne Disease Weekly*, p. 3, (Feb. 10, 1997).
Alan D. Henderson, Journal Article Summaries, *TBWeekly*, (Jan. 20, 1997).
K. Sato, et al., Antimicrobial Activities of Benzoxazinorifamycin KRM–1648, Clarithromycin and Levofloxacin Against Intracellular *Mycobacterium avium* Complex Phagocytosed by Murine Peritoneal Macrophages, *Journal of Antimicrobial Chemotherapy*, 41:77–83, (1998).
Haruaki Tomioka, et al., Therapeutic Efficacy Of Benzoxazinorifamycin, JRM–1648, Administered in Various Frequencies Per Week in *Mycobacterium Intracellulare*–Infected Mice, *Kekkaku*, 68(11):683–686 (1993).

* cited by examiner

*Primary Examiner*—Kevin E. Weddington
(74) *Attorney, Agent, or Firm*—Hana Verny

(57) ABSTRACT

A method for treatment of bacterial infections with rifalazil administered once-weekly or twice-weekly. A method for treatment of tuberculosis caused by *Mycobacterium tuberculosis*, infections caused by *Mycobacterium avium* complex, infections caused by *Chlamydia pneumoniae* and infections caused by *Helicobacter pylori* by administering to a patient suffering from the bacterial infection 1–100 mg of rifalazil once or twice a week. In this dose regimen, the treatment is fast, efficacious and eliminates undesirable secondary symptoms observed with daily doses of 1–50 mg of rifalazil.

16 Claims, 10 Drawing Sheets

METHOD FOR TREATMENT OF BACTERIAL INFECTIONS WITH ONCE OR TWICE-WEEKLY ADMINISTERED RIFALAZIL

BACKGROUND OF THE INVENTION

This application is based on and claims priority of Provisional Application Ser. No. 60/112,921 filed on Dec. 18, 1998.

FIELD OF THE INVENTION

The current invention concerns a method for treatment of bacterial infections with rifalazil administered once-weekly or twice-weekly. In particular, the invention concerns a method for treatment of tuberculosis caused by *Mycobacterium tuberculosis*, infections caused by *Mycobacterium avium* complex, infections caused by *Chlamydia pneumoniae* and infections caused by *Helicobacter pylori* by administering to a patient suffering from the bacterial infection rifalazil once or twice a week. In this dose regimen, the treatment is fast, efficacious and eliminates undesirable secondary symptoms observed with daily doses of 1–50 mg of rifalazil.

BACKGROUND AND RELATED DISCLOSURES

Bacterial infection caused by mycobacterium species and similar infections caused by *Chlamydia pneumoniae* or *H. pylori* cause serious health problems in the United States and worldwide. For example, tuberculosis, caused by *Mycobacterium tuberculosis* is one of the most serious infectious diseases outside of developed countries, with over one billion people infected worldwide. The worldwide infection rate results in eight million active tuberculosis cases annually and over two million deaths per year. In the United States, 26,000 near cases of active tuberculosis were reported in 1994. The number of active cases in the United States is high because of the increase in patients with AIDS and the increase in immigration from developing countries. Moreover, there is reported an increase in multidrug resistance tuberculosis and disseminated *Mycobacterium avium* complex infections.

Additionally, there is an increase in transmissible chlamydial diseases caused by *Chlamydia pneumoniae*, nonmotile, obligate intracellulare to bacteria. *Chlamydia pneumoniae* causes respiratory infections, such as pneumonia, bronchitis, pharyngitis and sinusitis, and has been associated with about 10% of community-acquired pneumonia. The *Chlamydia pneumoniae* infections are geographically wide spread. Studies on antibody prevalence have shown that large number of people is infected with *Chlamydia pneumoniae* at one time or another.

*Helicobacter pylori* infections are infections of gastrointestinal tract. *H. pylori* is a gram-negative microphilic organism residing in human stomach and intestine which is closely connected with acute gastritis and development of inflammation of mucous layer. Acute gastritis is associated with epigastric pain, nausea and vomiting. The organism is difficult to treat, delayed recurrences are frequent, and treatment involves multiple antibiotic regimens.

It would thus be highly advantageous to provide a method for treatment of the above-described diseases with new types of antibiotics which are able to efficaciously treat and/or eradicate the bacteria or organisms causing these diseases without necessity to utilize complex antibiotic treatments and, regimens which result in undesirable secondary symptoms and, adverse reactions.

It is, therefore, an object of this invention to provide a method for treatment of Mycobacterium species, *Chlamydia pneumoniae* and *H. pylori* infections with once a week or twice a week administration of a relatively new antibiotic, rifalazil, that belongs to the class of antibiotics called ansamycins. Rifalazil has the same or better activity than either rifabutin or rifampin, the other two antibiotics of the same class and actively inhibits the growth of *Mycobacterium tuberculosis*, *Mycobacterium avium* species, *Chlamydia pneumoniae* and *H. pylori* when administered only once a week or twice a week in doses from 1 to 50 mg. Previously, rifalazil has been administered on daily basis and because of the severe secondary adverse reactions, was discontinued as a drug for treatment of tuberculosis and other infection. Newly discovered once-week or twice-week regimen has the same efficacy as daily administration and yet eliminates or significantly decreases the adverse reactions.

Rifalazil compound has been described in the U.S. Pat. No. 4,983,602 where its antibacterial activity has been disclosed. Dosages described in vitro and in mice animal models correspond to a dose from 10 mg to 10 g/day for adults. However, when clinical trials with these doses of the antibiotic were administered daily, many adverse reactions occurred and the treatment with rifalazil was discontinued.

All patents, patent applications and publications cited herein are hereby incorporated by reference.

SUMMARY OF THE INVENTION

One aspect of the current invention is a method for treatment of bacterial infections with once or twice-week administration of rifalazil.

Another aspect of the current invention is a method for treatment of tuberculosis with once or twice-week: administration of rifalazil.

Still another aspect of the current invention is a method for treatment of *Mycobacterium avium* complex infections with once or twice-week administration of rifalazil.

Still another aspect of the current invention is a method for treatment of *Chlamydia pneumoniae* infections with once or twice-week administration of rifalazil.

Yet another aspect of the current invention is a method for treatment of *Helicobacter pylori* infections with once or twice-week administration of rifalazil.

DEFINITIONS

Figure 1:
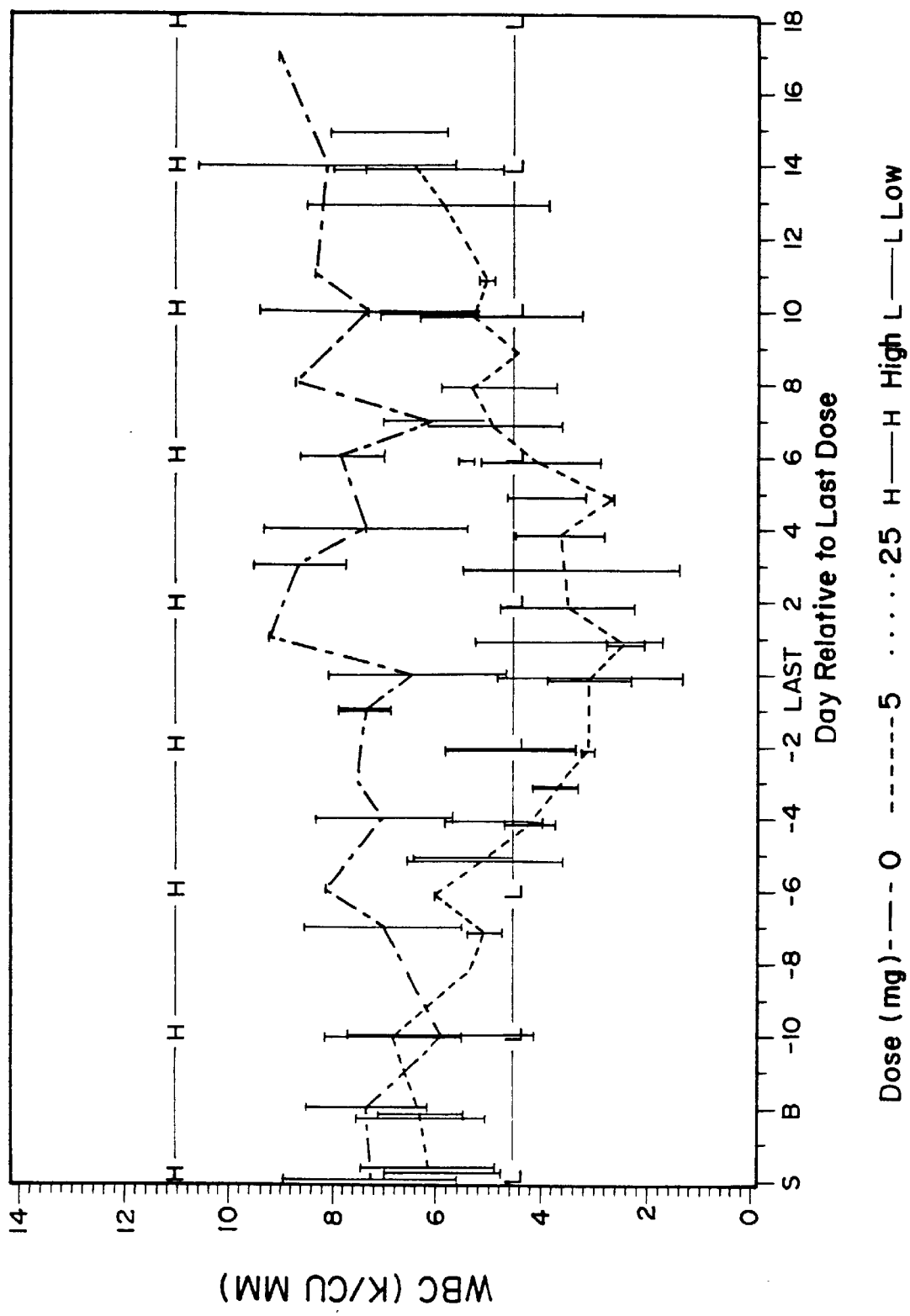
FIG. 1 illustrates decrease in white blood cells counts in daily dosing regimen used in a clinical trial on human volunteers where the daily dose of rifalazil was 5 or 25 mg compared to a control group receiving placebo.

"Rifalazil" means 3'-hydroxy-5'-(4-isobutyl-1-piperazinyl)benzoxasinorifamycin also known as KRM-1648.

"ANC" means absolute neutrophil count.

"ARS" means adverse reactions.

"$AUCO_{0-24}$" means area under the concentration time curve from 0 to 24 hours.

"$AUC_{0-\infty}$" means AUC from 0 hours to infinity.

"AZT" means azidodeoxythymidine.

"BID" means twice-a-day.

"BIW" means twice-a-week.

"BUN" means blood urea nitrogen.

"CFUs" means colony forming units.

"$C_{max}$" means maximum concentration.

"CL/F" means clearance (uncorrected for bioavailability).

"COSTART" means Coding Symbols for Thesaurus of Adverse Reaction Terms.

"CUM" means cubic micrometers.

"CYP" means cytochrome P450.

"ddC" means dideoxyctidine.

"EBA" means early bactericidal activity.

"EKG" means electrocardiogram.

"EMB" means ethambutol.

"G6PD" mean 5 glucose-6-phosphate dehydrogenase.

"GGT" means gamma glutamyl transpeptidase.

"IND" means Investigational New Drug.

"INH" means isoniazid.

"IP" means intraperitoneal.

"IRB" means Institutional Review Board.

"IV" or "i.v." means intravenous administration.

"$K_e$" means terminal rate constant.

"$K_a$" means absorption rate constant.

"K/CU MM" means thousands per cubic millimeter.

"LDH" means lactic dehydrogenase.

"LEV" means level of loxacin.

"M/CU MM" millions per cubic millimeter.

"MAC" means *Mycobacterial avium* complex.

"MBC" means minimum bactericidal concentration.

"MIC" means minimum inhibitory concentration.

"MTB" means *Mycobacterium tuberculosis*.

"*Mycobacterium avium* complex" means *Mycobacterium avium, Mycobacterium intracellulare, Mycobacterium marinum, Mycobacteruim kansasii,* and *Mycobacterium scrofulaceum*.

"NADPH" means nicotinamideadeninedinucleotide hydrogen phosphate.

"PT" means prothrombin time.

"PTT" means partial thromboplastin time.

"PZA" means pyrazinamide.

"RBT" means rifabutin.

"Rif" or "RMP" means rifampin.

"QID" means once a day.

"QIW" means once-a-week.

"SD" means standard deviation.

"SGOT (AST)" means glutamic oxaloacetic transaminase (aspartate transferase).

"SGPT (ALT)" means serum glutamic pyruvic transaminase, (alanine transferase).

"TB" means tuberculosis.

"$T_{max}$" means time to maximum concentration.

"$t_{1/2}$" means terminal half-life.

"$t_{1/2}$ abs" means half-life of absorption.

"UUG" means micro-microgram.

"$V_{beta}/F$" means volume associated with terminal phase; (uncorrected for biovailability).

"$V_{ss}/F$" means volume of distribution at steady state (uncorrected for bioavailability).

"WBC" means white blood cell.

DETAILED DESCRIPTION OF THE INVENTION

The current invention is based on findings and confirmation in vitro, in vivo and in clinical trials that: once-a-week or twice-a-week doses of 1–100, preferably 1–50 mg of rifalazil effectively treats bacterial infection without adverse reactions and without undesirable secondary symptoms observed with daily administration of this drug.

Although rifalazil was found to be effective against mycobacterium species, it has never been used as a therapeutic agent for treatment of mycobacterial diseases because at the daily dose regimen which was thought to be necessary to its efficacious antibacterial activity, rifalazil caused severe adverse reactions and secondary symptoms. The adverse reactions included flu-like symptoms with severe headache, malaise, fever, back pain, myalgia, chills, dizziness, nausea, vomiting, body pain and weakness. Additionally, the daily administration of rifalazil resulted in changes in blood cell counts, particularly in decrease of white blood cells counts (leukopenia), absolute neutrophil count and platelet count as well as in decreased blood hemoglobin. For these reasons, clinical studies involving daily dosing of rifalazil were abandoned.

It has now been found and is a subject of this invention that rifalazil in once-a-week or at most twice-a-week dosing regimen is effective in eradication of *Mycobacterium tuberculosis, Mycobacterium avium* complex, *Chlamydia pneumoniae* and *Helicobacter pylori* and for treatment of tuberculosis, *Mycobacterium avium* infections, psittacosis, lymphogranuloma venereum, trachoma, inclusion conjunctivitis; caused by *Chlamydia pneumoniae* and gastritis caused by *H. pylori*.

I. In Vitro and In Vivo Studies in Animal Models

Rifalazil and its related drugs rifampin and rifabutin, all belonging to a group collectively described as rifamycins, were known to exhibit antimicrobial activity against Mycobacterium species in vitro and in vivo animal models.

A. Physical, Chemical and Pharmaceutical Properties of Rifalazil

Rifalazil is 3'-hydroxy-5'-(4-isobutyl-1-piperazinyl) benzoxasinorifamycin of the chemical structure

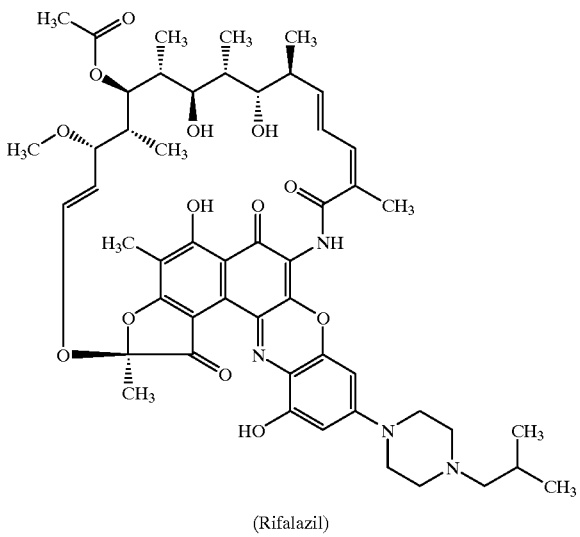

(Rifalazil)

Rifalazil is a member of the rifamycins, a complex group of antibiotics originally isolated from *Nocardia mediterranei* that exhibits antimicrobial activity against Mycobacteriun spp. The rifamycins belong to a class of antibiotics called. ansamycins, which contain macrocyclic, lactam bridges across non-adjacent (ansa) positions of an aromatic system.

Rifalazil is a nonpolar molecule that is stable and essentially insoluble in water. Two chemically-related drug substances rifampin and rifabutin are known to have similar biological activity.

Rifalazil synthesis is disclosed in U.S. Pat. No. 4,983,602, incorporated herein by reference in its entirety. Its known in vitro and in vivo activity is described in *Recent Res. Devel. Antimicrob. Agents Chemother.*, 2:37 (1997), aincorporated herein by reference. While these studies confirm the antibacterial activity of rifalazil in vivo as well as in vitro, such activity is based on daily administration of 2.5 and 5 mg of the drug to the mice infected with *M. tuberculosis*, corresponding to about 175 or 350 mg rifalazil dose/day/70 kg human.

Additionally, in vivo studies were performed where the therapeutically effective doses of rifalazil and rifampin were given at various intervals. When the dose 10 mg/kg (corresponding to 700 mg/70 kg human) six times a week was administered to treat *M. tuberculosis* infection induced in mice, there were no lesions observed in the lung and such treatment resulted in about 80% reduction of log CFU in lungs. Twice-a-week or once-a-week administration resulted in about 35% reduction of the bacteria and once-a-week administration of these very high dosages resulted in about 42% reduction in CFU. However, the used and documented doses were extremely and unphysioloqically high. For humans, the daily dose of rifalazil above 300 mg is unphysiological and even 50 mg of rifalazil administered to humans daily causes severe adverse reactions.

B. Nonclinical Studies

Rifalazil was extensively tested in vitro and in vivo in animal models and compared to other ansamycins, rifampin and rifabutin. The following is a brief description and summary of these studies.

1. Mechanism of Action

In vitro studies show that rifalazil acts on bacterial DNA-dependent RNA polymerase and inhibits the growth of aerobic and anaerobic gram-positive bacteria. However, rifalazil is relatively inactive against gram-negativet bacteria. This spectrum of activity is similar to rifampin and rifabutin, two related drugs.

Rifalazil is a potent inhibitor of many mycobacteriun Spp., including the *M. tuberculosis* (MTB) and *M. avium* complex (MAC), *Chlamydia pneumoniae* and *H. pylori*. Minimum inhibitory concentrations (MICs) of rifampin for MTB range from <0.002 to 4.0 µg/mL, depending on the degree of resistance to rifampin. When tested side by side against the same strains, the activity of rifalazil in vitro is consistently greater than either rifabutin or rifampin. Minimum bactericidal concentrations (MBCs) are typically 2–4 fold higher than the MICs.

The efficacy of rifalazil have been examined in vivo in macrophage and in animal models. Rifalazil readily accumulates in human macrophages and is bactericidal at concentrations equivalent to the MBCs established in vitro. In animal models of MTB infection, rifalazil was the most active single-agent against organisms in the spleen and lungs, although the combination of rifalazil and isoniazid (INH) or rifalazil and pyrazinamide (PZA) was more effective against organisms in the lung than either drug alone (*Antimicrobial Agents Chemotherapy*, 40: 298 (1996)).

The therapeutic effects of rifalazil are also long-lasting. For example, in mice infected with *M. intracellulare*, rifalazil significantly reduced the number of colony forming units (CFUs) in organs after four and eight. weeks of treatment and did so to a greater extent than rifabutin or rifampin. In a rabbit model of *M. avium* infection, rifalazil also reduced the bacterial load on organs compared to controls. Treatment of MTB infection in mice with rifalazil and INH for 12 weeks completely sterilized the lungs and spleens of infected animals and eliminated regrowth of the organisms for as long as 6 months post-treatment.

In chronic studies with dogs and rats, the no-observed-adverse-effect-level was 1000 mg/kg. The absolute bioavailability of $^{14}$C-rifalazil in rats at a dose of 3 mg/kg was 30 to 40%, but was reduced at higher doses. Rifalazil was slowly eliminated from the blood (mean terminal half-life of 12.5 hr) with a mean systemic clearance (CL/F) of 0.184 L/hr/kg in male rats and 0.217 L/hr/kg in female rats. Significant partitioning of drug-related radioactivity to the formed elements of the blood was observed. The principal routes of elimination appeared to be hepatic metabolism with the majority (84%) of the radioactivity recovered in the feces. The urine contained a small amount (5.5%) of radioactivity.

2. Rifalazil Antibacterial Activity in Vitro

The antimicrobial activity of rifalazil was measured in vitro against a variety of bacterial species. In vitro studies show that rifalazil inhibits the bacterial growth of aerobic and anaerobic gram-positive bacteria, but is relatively inactive against gram-negative bacteria. Rifalazil inhibits the growth of many Mycobacterium spp. (*Antimicrobial Agents Chemotherapy*, 35:542 (1991)), particularly the slower growing mycobacteria such as *M. tuberculosis, M. avium*, and *M. intracellulare*. Based on $MIC_{90}$ comparisons, as seen in Table 1, rifalazil was more active than rifampin.

TABLE 1

MIC$_{90}$ and Rifampin Against *Mycobacterium spp*

| | | MIC$_{90}$ (µg/mL) | |
|---|---|---|---|
| Species | No. of Strains | Rifalazil | Rifampin |
| *M. intracellulare* | 31 | 0.1 | 12.5 |
| *M. avium* | 18 | 1.56 | 100 |
| *M. tuberculosis* | 22 | 12.5 | 100 |

\* MIC determined by agar dilution method.
† RMP, rifampin.

The in vitro activity of rifalazil against *M. tuberculosis* has been determined by measuring the minimum inhibitory concentration (MIC) for a variety of clinical isolates and reference strains. The results of these studies are summarized in Table 2.

TABLE 2

Summary of In Vitro Susceptibility Studies for Rifalazil

| Ref. | MIC Method | No. Of Strains[1] | MIC Range (µg/mL) | MIC$_{90}$ (µg/mL) |
|---|---|---|---|---|
| 1 | BACTEC | 30 (rif$^r$ and rif$^s$) | ≦0.002 to 4.0 | 2.0 |
| 2 | BACTEC | 24 (rif$^r$ and rif$^s$) | 0.0009 to 4.0 | 4.0 |
| 3 | BACTEC | 13 (rif$^s$) | 0.0009 to 0.125 | 0.0156 |
| 4 | BACTEC | 11 (rif$^s$) | 0.062 to 4.0 | 4.0 |
| 5 | BACTEC | 20 (rif$^s$) | <0.125 | <0.125 |
| 6 | BACTEC | 20 (rif$^r$) | <0.125 to >2.0 | >2.0 |
| 7 | 7H11 agar | 22 (rif$^r$ and rif$^s$) | ≦0.0125 to 12.5 | 12.5 |
| 8 | 7H11 agar | 16 (rif$^s$) | Not available | ≦0.0125 |

[1]rif$^r$, rifampin-resistant; rif$^s$, rifampin-sensitive.

Ref. 1: *Antimicrobial Agents, Chemotherapy*, 39: 2295 (1995); Ref. 2–5: *Antimicrobial Agents, Chemotherapy*, 39:440(1995), Ref. 7 and 8: *Antimicrobial Agents. Chemotherapy*, 35: 542 (1991).

As seen in Table 2, rifalazil is more active than 25rifampin based on MIC$_{90}$ comparisons, however, the spectra of its antibacterial activities are similar to rifampin.

The in vitro activity of rifalazil against *M. tuberculosis* has been determined by measuring the minimumi inhibitory concentration (MIC) for a variety of clinical isolates and reference strains. The results of these studies are summarized in Table 3.

Studies described in *Antimicrobial Agents, Chemotherapy*, 39: 2295, (1995) determined the MICs of rifalazil against thirty clinical isolates and two stock cultures (H37Rv and Kurono) of *M. tuberculosis* (Table 3).

TABLE 3

MIC of Rifalazil, Rifabutin and Rifampin

| | MIC (µg/mL)[1] for | | | |
|---|---|---|---|---|
| | Clinical Isolates[2] | | Reference *M. tuberculosis* strain | |
| Drug | MIC50 50% inhibition | MIC90 90% inhibition | H37Rv | Kurono |
| Rifalazil | 0.016 | 2.0 | 0.004 | 0.002 |
| Rifabutin | 0.063 | 8.0 | 0.016 | 0.016 |
| Rifampin | 4.0 | >128.0 | 0.125 | 0.063 |

[1]MICs were determined by BACTEC method.
[2]Thirty strains were tested.

Table 3 shows Minimum Inhibitory Concentrations (MICS) of rifalazil, rifabutin and rifampin for clinical isolates and two reference strains of *Mycobacterium tuberculosis*.

As seen in Table 3, rifalazil had more than a 64-fold greater activity than rifampin and a 4-fold greater, activity than rifabutin based on comparisons of the MIC$_{50}$ and MIC$_{90}$. This increased activity of rifalazil was also observed with the reference strains. An examination of the individual MICs of the thirty isolates shows that rifalazil was more active than rifampin in all thirty isolates and more active than rifabutin in twenty-eight isolates.

The MIC and NBC of rifalazil against extracellular *M. tuberculosis* and *M. tuberculosis* in human macrophages using strains H37Rv, Erdman, and Atencio were described in *Antimicrobial Agents, Chemotherapy*, 409:1482 (1996). Extracellular and intracellular bacteria were exposed to varying concentrations of rifalazil for 7 or 8 days, macrophages were lysed where applicable, then the CFUs werea determined by plating on agar. The MIC was defined as the 16 lowest concentration of rifalazil that inhibited more than 99% of the growth following the drug-incubation period. The MBC was defined as the lowest concentration of rifalazil that killed more than 99% of the bacteria following the drug-incubation period. The results of the study show that the MIC and MBC of rifalazil are at least 10-fold lower than rifampin for both intracellular and extracellular bacteria (Table 4).

TABLE 4

Minimum Inhibitory Concentration (MIC) and Minimum Bactericidal Concentration (MBC) of Rifalazil and Rifampin (RMP) Against *Mycobacterium tuberculosis* Strains

| | Concentration (µg/mL) | | | | | | | |
|---|---|---|---|---|---|---|---|---|
| | Intracellulare Bacteria | | | | Extracellular Bacteria | | | |
| | Rifalazil | | Rifampin | | Rifalazil | | Rifampin | |
| Strain | MIC | MBC | MIC | MBC | MIC | MBC | MIC | MBC |
| H37Rv | 0.004 | 0.016 | 0.25 | 1.0 | 0.008 | 0.031 | 0.12 | 0.5 |
| Erdman | 0.008 | 0.008 | 0.12 | 0.5 | 0.002 | 0.004 | 0.12 | 0.5 |
| Atencio | 0.004 | 0.008 | 0.25 | 0.5 | 0.001 | 0.008 | 0.25 | 0.25 |

*Antimicrobial Agent, Chemother.*, 40:1482 (1996).

3. Rifalazil Antibacterial Activity In Vivo

The therapeutic effect of rifalazil was examined by measuring gross lung lesions, bacterial loads, and survival time in mice infected with *M. tuberculosis* and subsequently treated with rifalazil or rifampin for eight weeks (*Antimicrobial Agents, Chemotherapy*, 39: 2295 (1995)). In each of these tests, rifalazil outperformed rifampin in treating the disease.

The activity of rifalazil alone and in combination with other drugs in mice infected with the rifampin-sensitive *M. tuberculosis* strain Erdman (MIC$_{rif}$=0.06 kg/mL) was examined and results are described in *Antimicrobial Agents Chemotherapy*, 38: 2245 (1994). Treatment was started one week after infection, and drug was administered five times per week for four weeks. Control mice were sacrificed at the start of treatment (early controls) and four weeks later (late controls).

Initial experiments compared the ability of rifalazil, rifabutin, or rifampin (all at 20 mg/kg) to reduce the bacterial load in lungs and spleens of infected mice compared to untreated mice. Rifalazil reduced bacterial loads to a significantly greater extent than the other two drugs (P<0.01). No significant differences were observed between rifabutin and rifampin (P>0.05).

Additional experiments examined the ability of rifalazil (20 mg/kg) alone and in combination with INH (isoniazid, mg/kg), PZA (pyrazinamide, 150 mg/kg), EMB (ethambutol, 125 mg/kg), or LEV (level of loxacin, 200 mg/kg) to reduce this bacterial load in lungs and spleens of infected mice.

Treatment with all drugs significantly reduced CFUs irn the spleen compared to controls, except for PZA. PZA did not significantly reduce CFUs compared to controls. Rifalazil was the most active single-agent against organisms in the spleen. Only the combination of rifalazil plus PZA was more active than rifalazil alone.

In lungs, treatment with rifalazil or INH significantly reduced cell counts in lungs compared to early controls. Compared to late controls, treatment with rifalazil, INH, EMB, or LEV reduced cell counts in lungs. Rifalazil was the most active single-agent. The combinations of rifalazil plus INH or rifalazil plus PZA were more active against organisms in lungs than treatment with rifalazil alone.

In a subsequent study, the treatment period was extended from 4 weeks to 12 weeks and the regrowth of organisms in spleen and lung was measured for 24 weeks post-treatment. The combination of rifalazil (20 mg/kg) and INH (25 mg/kg) was significantly more effective at reducing the number of CFUs in spleens and lungs of mice compared to rifalazil alone (20 mg/kg), INH alone (25 mg/kg), rifampin alone (20 mg/kg), and the combination of rifampin and INH (20 mg/kg and 25 mg/kg, respectively).

4. In Vitro and In Vivo Activity Against Other Bacteria

Rifalazil activity was also tested on other bacteria and organisms. Rifalazil shows a strong antibacterial activity against Chlamydia pneumoniae and against Helicobacter pylori.

Sensitivity testing was conducted in cell cultures3 against Chlamydia pneumoniae strain TW-1 83 using rifalazil, clanthromycin, or azithromycin. In these studies, rifalazil was 300-fold more potent than clanthromycin and 1500-fold more potent than erythromycin. The in vivo testing of rifalazil used a mouse model infected with Chlamydia pneumoniae strain AR-39. The results showed that Chlamydia pneumoniae was not detectable from the lungs of an animal five days after the cessation of rifalazil treatment by intraperitoneal injection of rifalazil at 1 mg/kg QID for three days. All control animals remained infected.

Rifalazil bactericidal activities were also evaluated in vitro against twenty-four strains of Helicobacter pylori. In these studies, rifalazil exhibited more potent antimicrobial activities against Helicobacter pylori than amoxicillin and rifampin. Time-kill studies, described in Abstract, 4th Japan-Korea International Symposium on Microbiology, Takashimaya, Japan, Oct. 22–23 (1998), revealed that the CFUs at 24 hours in the broth medium containing rifalazil at 0.04 mg/mL were more than 4.5 log lower than the control at zero hours, indicating rifalazil's potent bactericidal activity. Under the same conditions amoxicillin at 0.31 mg/mL produced only 1 log decrease in CFU/mL after 24 hours.

Results described above indicate that rifalazil has ver-y good antibacterial activity and is a better choice of the drug for treatment of bacterial infections caused by Chlamydia pneumoniae and Helicobacter pylori.

5. Pharmacology of Rifalazil

Pharmacological studies were undertaken in mice, rats, and dogs, and in isolated guinea pig ileum. The preclinical pharmacology data showed that rifalazil has no important central/autonomic nervous system, respiratory, cardiovascular, digestive system, or renal pharmacological effects.

Rifalazil had little effect on the clinical signs or general behavior of mice following oral administration of 100, 300, or 1,000 mg/kg. Rifalazil had no effect on the spontaneous locomotor activity of mice at 100 and 300 mg/kg. At 1000 mg/kg, rifalazil caused an increase in spontaneous locomotor activity for one hour.

6. Pharmacokinetics of Rifalazil

Pharmacokinetic parameters were determined following single and multiple doses in rats and dogs. The doses in rats and dogs were based upon those utilized in the single and multiple-dose toxicology studies. In addition, the absorption, distribution, metabolism, and elimination of rifalazil was studied in rats and dogs. These studies confirmed prior findings that there are species differences vis-a-vis sensitivity to and response to treatment with rifalazil.

Preclinical pharmacokinetic data in rats and dogs showed that the disappearance of rifalazil and/or metabolites from whole blood is slow and that significant whole blood concentrations can be achieved following repeated oral administration. Upon repeated dosing, a slight increase in rifalazil $C_{max}$ and AUC values was observed in rats and dogs. Such increase was consistent with the drug accumulation. Significant metabolism of rifalazil through deacetylation in both dogs and rats and hydroxylation in dogs only, occurred in both single and multiple-dose studies. In addition, significant accumulation of both metabolites was observed following repeat rifalazil dosing in dogs.

7. Toxicology of Rifalazil

Single-dose and multiple-dose oral toxicology studies were conducted in mice, rats, and dogs. In addition, to maximize systemic exposure, single-dose intravenous (IV) and intraperitoneal (IP) studies were conducted in rats and mice. Four-week and 13-week oral studies in dogs and rats and 26-week oral studies in rats included standard clinical measurements and physical and pathological evaluations.

Under the conditions of these studies, rifalazil was relatively well-tolerated in animal models following single or multiple-dose oral administration. Hematological changes were noted following a multiple-dose oral administration at doses >30 mg/kg in both rats and dogs. Aside from the slight increase in liver weight in dogs at 1,000 mg/kg, there was no evidence of any significant systemic target organ changes following four weeks of daily dosing in dogs and rats at doses approximately 100 times the highest projected clinical dose on a mg/kg basis.

In the 26-week study, a dose-related lymphocytic depletion in the spleens of rats administered >30 mg/kg/day was observed. Lower absolute and relative spleen weights in these animals correlated with this apparent loss of lymphocytes. Lymphoid depletion in the spleens of treated animals and decreased peripheral blood lymphocyte count show that at certain concentration, rifalazil causes adverse reactions. However, there was no evidence that the animals in this study were immunosuppressed, as no opportunistic infection were observed.

The 13-week study of daily oral administration of rifalazil to dogs demonstrated that the "no observable adverse effect level" was considered to be 300 mg/kg for dogs. Lower lymphocytic counts were not reversed within four weeks after treatment, and therefore, the long-term consequences of this effect in dogs are unknown.

These and other findings in mice demonstrate that there is clear species difference in adverse reactions response between animals and humans. While in mice, rats, and dogs rifalazil dosages over 300 mg/kg were well tolerated in long-term studies, such tolerance was not found in human volunteers. The dose 300 mg/day caused severe adversie reactions and daily dosing at this level could not be continued. The doses of 25, 50 and 100 mg/day also caused severe adverse reactions in human volunteers.

The species differences between animals and human is therefore well documented and shows that the experimental results obtained in laboratory animals cannot be extrapolated for humans.

II. Clinical Studies

Clinical studies were conducted both on healthy volunteers and on patients diagnosed with tuberculosis.

A. Safety, Pharmacokinetics and Toxicity of Rifalazil in Healthy Volunteers

1. Clinical studies Design

A total of four clinical trials have been conducted to study the effects of rifalazil in humans. Two single-dose Phase 1 clinical trials (001) and (002) assessed the safety and pharmacokinetics of rifalazil in normal, healthy, fasted subjects. In the 001 trial, a single 300 mg dose of rifalazil was administered to six subjects. In the 002 trial, single doses of 30 mg or 100 mg were administered to eight subjects each. The results of these studies indicated a substantially higher incidence of adverse reactions at the 300 mg dose compared to the 30 mg or 100 mg dose.

The third (003) and fourth (004) Phase 1 clinical trials were multiple-dose studies. Because evidence from animal studies showed increased bioavailability when rifalazil was administered with food, the clinical trials were designed to further assess the safety and pharmacokinetics of rifalazil in fed, normal, healthy subjects.

The third trial (003) was a randomized, rising, double-blind, multiple-dose, placebo-controlled study where subjects were observed during the 14-consecutive days of drug administration in dosages 0, 5 and 25 mg/day and for an additional 14 days without medication. All subjects received the dose within 30 minutes after eating a standardized breakfast. Subjects were divided into two groups. In Group 1, eight subjects were randomized to a daily 25 mg dose oif rifalazil and four subjects were randomized to placebo. Numerous adverse reactions began to appear with the 25 mg dose several days after dosing and it became apparent that 25 mg daily dose was not safe. Consequently, after review of the safety data, the study protocol was amended to proceed with a lower dose of 5 mg in group 2. Group 2 consisted of eight subjects randomized to a daily 5 mg dose of rifalazil and four subjects randomized to placebo.

The fourth trial (004) was a also a randomized, rising, double-blind, multiple-dose, placebo-controlled study. In this trial, weekly doses of placebo or rifalazil (25 mg or 50 mg) were administered to the subjects for a total of 4 weeks. All subjects received the dose within 30 minutes after eating a standardized breakfast and were monitored for an additional 14 days after the last dose. Four subjects were randomized to placebo, six subjects to 25 mg rifalazil, and eight subjects to 50 mg rifalazil.

Both the third and fourth Phase 1 studies included a 14-day period without medication following the last dose to observe the number and severity of adverse reactions, and the time to resolution. Safety was assessed by physical examination, monitoring vital signs and cardiac function, measurement of clinical laboratory values in blood, serum, and urine, and by documenting adverse reactions. Systemic drug levels were measured in each dose group.

2. Adverse Reactions Observed After Rifalazil Administration to Healthy Subjects Most of the adverse reactions in all four Phase 1 studies were considered to be related to the study drug. The most common adverse reaction in all studies was headache. Other commonly reported adverse reactions, which collectively included "flu-like" symptoms, included fever, back pain, chills, dizziness, nausea, vomiting, body pain, and weakness. These "flu-like" symptoms have been also described for two other related rifamycins, rifampin and rifabutin.

Vital signs and physical assessments were within normal parameters and did not change throughout any study. All EKG findings were coded as clinically insignificant and were normal, near-normal, or borderline normal.

3. Single-Dose Study—Clinical Trials 001 and 002

In the first (001) and second (002) clinical trials, adverse reactions, change in laboratory parameters and pharmacokinetic of rifalazil were observed in healthy volunteers receiving dosages of 30 mg, 100 mg and 300 mg of rifalazil.

Results are seen in Table 5 which shows a comparative summary of the number of subjects reporting unique adverse reactions observed in clinical trials 001 and 002. As seen in Table 5 a substantially greater number of subjects reported adverse reactions with the 300 mg dose compared to the 30 and 100 mg doses.

TABLE 5

Adverse Reactions in Healthy Volunteers

| | | Rifalazil Study | | | | |
| --- | --- | --- | --- | --- | --- | --- |
| | | 001 | 002 | | | 001 and 002 |
| | | Dose | | | | |
| Body System[1] | Adverse Reactions | 300 mg n = 6 | 0 mg n = 9 | 30 mg n = 8 | 100 mg n = 8 | All Doses n = 31 |
| N of Subjects with any AE | | 4 | 2 | 3 | 1 | 10 |
| N of Subjects with any AE | | 2 | 7 | 5 | 7 | 21 |
| Body | Abdominal Pain | 1 | 0 | 0 | 0 | 1 |
| | Asthenia | 2 | 0 | 0 | 1 | 3 |
| | Back Pain | 2 | 0 | 0 | 0 | 2 |
| | Fever | 3 | 0 | 0 | 1 | 4 |
| | Headache | 3 | 0 | 3 | 1 | 4 |
| | Malaise | 1 | 0 | 0 | 0 | 1 |
| | Pain | 1 | 0 | 0 | 0 | 1 |
| CV | Tachycardia | 3 | 0 | 0 | 0 | 3 |
| | Vasodilation | 0 | 1 | 1 | 1 | 3 |
| DIG | Abnormal Stools | 1 | 0 | 0 | 0 | 1 |
| | Anorexia | 1 | 0 | 0 | 0 | 1 |
| | Dyspepsia | 1 | 0 | 0 | 0 | 1 |
| | Vomiting | 1 | 0 | 0 | 0 | 1 |
| NER | Dizziness | 1 | 0 | 0 | 0 | 1 |
| | Paraesthesia | 1 | 0 | 0 | 0 | 1 |
| | Somnolence | 1 | 0 | 0 | 0 | 1 |
| RES | Pharyngitis | 2 | 0 | 0 | 0 | 2 |
| SKIN | Dry Skin | 1 | 0 | 0 | 0 | 1 |
| | Sweating | 1 | 0 | 0 | 0 | 1 |
| SS | Taste Prevision | 1 | 0 | 0 | 0 | 1 |

[1]BODY: body as a whole; CV: cardiovascular system; DIG: digestive system; NER: nervous system; RES: respiratory system; SKIN: skin and appendages; SS: special senses.

When the obtained adverse reactions were evaluated by severity, i.e., mild adverse reactions, moderate reactions and severe reactions, as seen in Table 6, both the number and severity of drug-related adverse reactions were found to increase with a dose. Regardless of the dose, all adverse reactions resolved within two weeks of drug discontinuation istration of single doses of 30 mg, 100 mg, or 300 mg of rifalazil in these studies.

TABLE 6

Number and Severity of Drug-Related Adverse Reactions in 001 and 002 Clinical Trials

| Study | Dose | N of subjects | Severity | | | ARs |
|---|---|---|---|---|---|---|
| | | | Mild | Moderate | Severe | |
| 001 | 300 mg | 6 | 41 | 8 | 4 | 53 |
| 002 | 0 mg | 9 | 2 | 0 | 0 | 2 |
| | 30 mg | 8 | 4 | 0 | 0 | 4 |
| | 100 mg | 8 | 5 | 2 | 0 | 7 |
| TOTAL | | 31 | 52 | 10 | 4 | 66 |

As seen in Table 6, 300 mg dose of rifalazil resulted in forty-one mild, eight moderate and four severe adverse reactions. In contrast, placebo, 30 or 100 mg doses resulted in two, four or five mild adverse reactions ahd in zero, zero and two moderate adverse reactions, respectively. No severe adverse reactions were observed for placebo and for both 30 and 100 mg dose groups.

In the clinical trials 001 and 002 all patients were submitted to laboratory testing where the hematology, serum chemistry and urinanalysis were examined prior to dosing, during dosing and at least 14 days following the cessation of drug administration.

In these two trials, white blood cell (WBC) counts, absolute neutrophil counts (ANC), platelet counts, and blood hemoglobin were decreased in a dose-dependent manner. These parameters returned to the normal range within 14 days of final administration of rifalazil, and were noted to be similar to effects produced by other rifamycins.

The pharmacokinetics of rifalazil in whole blood in these two clinical trials was similar to that of rifalazil pharmacokinetics in plasma. Converse to data generated from animal studies, human subjects demonstrated a higher (1.6:1) plasma to blood ratio. Therefore, future pharmacokinetic analyses focused on rifalazil concentrations in plasma. Table 7 summarizes noncompartmental parameters derived from plasma concentrations in fasted subjects following admin-

TABLE 7

Comparison of Noncompartmental Pharmacokinetic Parameters Derived from Plasma Concentrations in Single Dose Studies 001 and 002

| Parameters (mean) | Trial and Dose | | |
|---|---|---|---|
| | Rifalazil - 001 | Rifalazil - 002 | |
| | 300 mg | 100 mg | 30 mg |
| Tmax (h) | 3.0 | 4.0 | 3.1 |
| Cmax (ng/mL) | 115.7 | 58.6 | 17.8 |
| Half-life (h) | | | |
| distribution $t_{1/2}$ | — | — | — |
| elimination $t_{1/2}$ | 205.6 | 43.1 | 48.7 |
| AUC (ng.h/mL) | | | |
| 0–24 | 1454.6 | 800.4 | 196.9 |
| 0–∞ | 4329.4 | 1543.3 | 504.9 |

4. Multiple-Dose Study—Clinical Trials 003 and 004

In the third (003) and fourth (004) clinical trials, adverse reactions, change in laboratory parameters and pharmacokinetics of rifalazil were observed.

A comparative summary of the number of subjects reporting unique adverse reactions observed in clinical trails 003 and 004 appears in Table 8.

TABLE 8

Adverse Reactions in Single-Dose and Multiple Dose Trials

| Body System[1] | Adverse Reactions | Study | | | | | |
|---|---|---|---|---|---|---|---|
| | | Rifalazil-003 | | Rifalazil-004 | | Rifalazil-003/004 | |
| | | 5 mg/day (n = 8) | 25 mg/day (n = 8) | 25 mg/wk (n = 6) | 50 mg/wk (n = 8) | 0 mg (n = 13) | All Doses (n = 43) |
| | N of Subjects with Any AE | 8 | 8 | 5 | 8 | 6 | 35 |
| | N of Subjects with No AE | 0 | 0 | 1 | 0 | 7 | 8 |
| BODY | Abdominal Pain | 1 | 1 | 0 | 0 | 0 | 2 |
| | Asthenia | 0 | 3 | 2 | 2 | 1 | 8 |
| | Back Pain | 6 | 7 | 3 | 4 | 0 | 20 |
| | Chills | 2 | 4 | 3 | 5 | 0 | 14 |
| | Fever | 2 | 6 | 4 | 7 | 1 | 20 |
| | Headache | 5 | 8 | 4 | 7 | 3 | 27 |
| | Neck Pain | 0 | 0 | 1 | 2 | 0 | 3 |
| | Pain | 6 | 5 | 3 | 6 | 1 | 21 |
| CV | Vasodilatation | 0 | 3 | 0 | 3 | 1 | 7 |
| DIG | Anorexia | 1 | 1 | 1 | 2 | 0 | 5 |
| | Diarrhea | 1 | 2 | 0 | 0 | 0 | 3 |
| | Dry Mouth | 1 | 1 | 0 | 0 | 0 | 2 |

TABLE 8-continued

Adverse Reactions in Single-Dose and Multiple Dose Trials

| | | Study | | | | | |
|---|---|---|---|---|---|---|---|
| | | Rifalazil-003 | | Rifalazil-004 | | Rifalazil-003/004 | |
| Body System[1] | Adverse Reactions | 5 mg/day (n = 8) | 25 mg/day (n = 8) | 25 mg/wk (n = 6) | 50 mg/wk (n = 8) | 0 mg (n = 13) | All Doses (n = 43) |
| | Dyspepsia | 1 | 1 | 0 | 1 | 1 | 4 |
| | Mouth Ulceration | 0 | 0 | 1 | 0 | 0 | 1 |
| | Nausea | 0 | 5 | 1 | 2 | 0 | 8 |
| | Thirst | 0 | 0 | 1 | 1 | 0 | 2 |
| | Vomiting | 0 | 2 | 1 | 2 | 0 | 5 |
| MS | Arthralgia | 1 | 0 | 0 | 0 | 0 | 1 |
| | Myalgia | 0 | 3 | 0 | 1 | 0 | 4 |
| NER | Dizziness | 0 | 4 | 3 | 3 | 1 | 11 |
| | Insomnia | 0 | 0 | 2 | 1 | 0 | 3 |
| | Somnolence | 0 | 0 | 0 | 1 | 0 | 1 |
| RES | Pharyngitis | 0 | 1 | 0 | 0 | 0 | 1 |
| | Rhinitis | 0 | 2 | 0 | 0 | 0 | 2 |
| SKIN | Pruritus | 0 | 1 | 0 | 0 | 0 | 1 |
| | Dry Skin | 0 | 0 | 1 | 0 | 0 | 1 |
| | Sweating | 0 | 1 | 0 | 1 | 0 | 2 |
| SS | Conjunctivitis | 1 | 0 | 0 | 0 | 0 | 1 |
| | Eye Pain | 2 | 3 | 0 | 0 | 0 | 5 |
| | Taste Perversion | 0 | 2 | 0 | 0 | 0 | 2 |

BODY: body as a whole; CV: cardiovascular system; DIG: digestive system; MS: musculo-skeletal system; NER: nervous system; RES: respiratory system; SKIN: skin and appendages; SS: special senses.

As seen in Table 8, more subjects reported adverse reactions with regimens of higher dose and/or shorter dosing intervals. Also, more frequent episodes of the unique adverse reactions appeared with the higher dose regimens.

Table 9 displays the most frequently reported adverse reactions which were reported 28 times in either study for 003 and 004 trials. All these adverse reactions are considered "flu-like" symptoms.

the number of adverse reactions in the same dose regimen (25 mg) decreased substantially from thirteen to eight for fever, from nineteen to eleven for headache and from fourteen to five for backpain.

These results clearly show that once a week dosage of rifalazil has much lower incidence of adverse reactions.

TABLE 9

Adverse Reactions Observed in 003 and 004 Clinical Trials

| | Study | | | | | | |
|---|---|---|---|---|---|---|---|
| | Rifalazil 003 | | | | Rifalazil 004 | | |
| Adverse Reactions | 0 mg (Placebo) | 5 mg /day | 25 mg /day | All doses | 0 mg (Placebo) | 25 mg /wk | 50 mg /wk | All Doses |
| Asthenia | 0 | 0 | 3 | 3 | 1 | 5 | 2 | 8 |
| Chills | 0 | 4 | 8 | 12 | 0 | 3 | 9 | 12 |
| Dizziness | 0 | 0 | 10 | 10 | 1 | 3 | 6 | 10 |
| Fever | 0 | 7 | 13 | 20 | 1 | 8 | 19 | 28 |
| Headache | 1 | 10 | 19 | 30 | 2 | 11 | 33 | 46 |
| Nausea | 0 | 0 | 8 | 8 | 0 | 1 | 4 | 5 |
| Pain (back) | 0 | 7 | 14 | 21 | 0 | 5 | 5 | 10 |
| Pain (body) | 0 | 2 | 5 | 7 | 1 | 3 | 13 | 17 |
| Pain (eye) | 0 | 5 | 3 | 8 | 0 | 0 | 0 | 0 |

[1]Defined as >8 reports/event in either study.
[2]Pain terms not grouped to allow differentiation.

As shown in Table 9, for both daily multiple-dose 003 and once-a-week multiple dose 004 clinical trials, adverse reactions were dose dependent with the highest incidence of fever, headache and back pain, observed in the clinical trial 003 where the drug was administered daily. When the multiple-dose of rifalazil 25 mg/weekly was administered, In Tables 8 and 9, the clinical trial 003 are compared to clinical trial 004, in terms of the adverse reactions associated with daily dosing of rifalazil. In Tables 10 and 11, the number of drug-related adverse reactions and severity of these reactions associated with daily dosing is shown vis-a-vis each subject and each dose for 003 clinical trial.

TABLE 10

Number of Adverse Reactions in 003 Clinical Trial

| Group | Dose | Subject Number | Number of Drug-Related ARs |
|---|---|---|---|
| 1 | 0 mg (Placebo) | 01 | 0 |
| | | 06 | 0 |
| | | 07 | 0 |
| | | 09 | 1 |
| | | Total | 1 |
| 1 | 25 mg/day | 02 | 16 |
| | | 03 | 21 |
| | | 04 | 19 |
| | | 05 | 3 |
| | | 08 | 9 |
| | | 10 | 17 |
| | | 11 | 12 |
| | | 12 | 15 |
| | | Total | 112 |
| 2 | 0 mg (Placebo) | 01 | 0 |
| | | 05 | 0 |
| | | 07 | 1 |
| | | 09 | 0 |
| | | | 0 |
| | | Total | 1 |
| 2 | 5 mg/day | 02 | 4 |
| | | 03 | 4 |
| | | 04 | 3 |
| | | 06 | 6 |
| | | 08 | 26 |
| | | 10 | 3 |
| | | 11 | 5 |
| | | 12 | 1 |
| | | Total | 52 |

As seen in Table 10, at daily dosing with 25 mg of rifalazil, subjects experienced total of one hundred and twelve adverse reactions while at the daily dose of 5 mg, 8 subjects experienced total of fifty-two adverse reactions. Placebo groups experienced only one adverse reaction each. This study clearly show that multiple-dosages of rifalazil are dose dependent and that even a relatively small dosage of 5 mg of rifalazil daily cause substantial increase in adverse reactions compared to placebo.

Table 11 shows the number and severity of drug-related adverse reactions observed in the 003 clinical trial.

TABLE 11

Severity of Adverse Reactions in 003 Clinical Trial

| | | Severity | |
|---|---|---|---|
| Group | Dose | Mild | Moderate |
| 1 | 0 | 1 | 0 |
| | 25 mg/day | 102 | 10 |
| 2 | 0 | 1 | 0 |
| 2 | 5 mg/day | 46 | 6 |
| TOTAL | | 150 | 16 |

As seen in Table 11, severity of the adverse reactions was also dose-dependent. When the dosage of 25 or 5 mg of rifalazil was administered daily, one hundred and two and forty-six mild adverse reactions and ten and six moderate adverse reactions were observed. With the higher 25 mg/day dosage, the number of adverse reactions was more than double for mild reactions and almost double for moderate reactions.

As seen in Tables 10 and 11, in Group 2 (5 mg/day), all eight subjects receiving drug reported at least one adverse reaction, compared to one of four placebo subjects. By Day 7, five subjects continued to receive rifalazil while three subjects dropped from the study because of adverse reactions. By Day 10, only one subject was still receiving drug. Dosing was suspended after Day 11 by the site investigator. Daily administration of rifalazil was, therefore, found to be unacceptable to the subjects and such daily administration had, to be discontinued.

Most adverse reactions observed in the 003 clinical trial were categorized as mild, except for 16 events (16/166 or 9.6%) rated as moderate as seen in Table 11. Ten of these moderate events occurred among two subjects in Group 1 (25 mg/day). Seven of the eight subjects receiving drug discontinued the study due to experiencing a "flu-like" symptoms. Five of these subjects also had a concurrent, clinically significant decrease in white blood cell count (WBC).

In Group 2 (5 mg/day), all eight subjects receiving drug reported at least one adverse reaction compared to one of four placebo subjects (Table 10). The total number of adverse reactions reported was half the incidence of Group 1. In addition, the number of unique adverse reactions experienced per patient was also about half the number in Group 2 versus Group 1. Five of the eight subjects receiving rifalazil completed the study. Three subjects dropped due to adverse reaction. One subject experienced half of all the recorded adverse reactions for Group 2 (26/52, see Table 10). This subject also experienced all of the six adverse reactions that were graded moderate in severity within Group 2 (Table 11). Although three of the eight subjects receiving rifalazil reported a mild, "flu-like" symptoms, only one of these subjects discontinued the study early. All three subjects experiencing the "flu-like" symptoms had concurrent, clinically significant decreases in WBC.

In clinical trial 004, specifically, the adverse reactions associated with weekly dosing of rifalazil are listed in Tables 8 and 9, and compared to 003 trial results. Tables 12 and 13 show the number and severity of drug-related adverse reactions associated with once-a-week administration of rifalazil vis-a-vis each subject and each dose in 004 clinical trial.

TABLE 12

Number of Adverse Reactions in 004 Clinical Trial

| Dose | Subject Number | Number of Drug-Related ARs |
|---|---|---|
| 0 mg (Placebo) | 02 | 2 |
| | 04 | 1 |
| | 07 | 1 |
| | 14 | 3 |
| | Total | 7 |
| 25 mg/wk | 08 | 0 |
| | 10 | 17 |
| | 12 | 6 |
| | 13 | 16 |
| | 15 | 4 |
| | 18 | 3 |
| | Total | 46 |
| 5 mg/day | 01 | 5 |
| | 03 | 7 |
| | 05 | 21 |
| | 06 | 20 |
| | 09 | 3 |
| | 11 | 16 |

TABLE 12-continued

Number of Adverse Reactions in 004 Clinical Trial

| Dose | Subject Number | Number of Drug-Related ARs |
|---|---|---|
|  | 16 | 30 |
|  | 17 | 13 |
|  |  | Total 115 |

As seen in Table 12, the number of adverse reactions observed following once-a-week administration of rifalazil to healthy volunteers was directly related to the dosage of rifalazil administered. When the dosage was 25 mg/week, there were forty-six adverse reactions. When the dosage was 50 mg/week, then there were one hundred and fifteen adverse reactions, almost 2.5 times more.

Table 13 shows a number and severity of drug-related adverse reactions observed in 004 clinical trial.

TABLE 13

Severity of Adverse Reactions in 004 Clinical Trial

| Dose | Severity | | |
|---|---|---|---|
|  | Mild | Moderate | Severe |
| 0 mg (Placebo) | 7 | 0 | 0 |
| 25 mg/wk | 40 | 6 | 0 |
| 50 mg/wk | 93 | 21 | 1 |
| TOTAL | 140 | 27 | 1 |

Details of the adverse reactions associated with weekly dosing of rifalazil appear in Tables 8, 9, 12 and 13. All eighteen subjects completed the 004 clinical trial. Fewer unique adverse reactions were reported per subject in the 25 mg group, versus the 50 mg group. There again appeared to bet is a dose-related incidence of adverse reactions. More than twice the number of adverse reactions were reported by subjects in the 50 mg group as compared to the 25 mg group (Table 12). Seven adverse reactions were reported by those receiving placebo. One patient in the 25 mg group reported no adverse reactions. The cluster of reported adverse reactions remained similar to other studies. As seen in Table 13, most adverse reactions (140/168, 83%),were classified as mild in severity. Only six adverse reactions were rated as moderate in the 25 mg group, compared to 21 moderate adverse reactions and one severe adverse reaction in the 50 mg group. One subject in the 50 mg group experienced 30 adverse reactions, twenty of which were graded as mild, nine moderate, and one severe.

Laboratory testing regimen for 003 and 004 trials was the same as for 001 and 002 trials.

Abnormal laboratory values were observed at various times during both 003 and 004 trials in three hematologic parameters: in platelet count, in white blood cells (WBC) counts, and in absolute neutrophil counts (ANC). Serum chemistry data revealed minor abnormalities in serum glucose, and liver function tests (SGOT, SGPT, GGT, and LDH) which were not considered to be clinically relevant upon initial review. With the exception of elevated liver function tests in two subjects receiving placebo in 003 clinical trial, all other laboratory measurement remained within the normal established ranges. In clinical trial 003, all subjects in Group 1 receiving 25 mg of rifalazil/day discontinued the study early.

The onset and magnitude of decrease in hematologic parameters appeared to be related to this dose. In order to better visualize the drop and subsequent recovery in these parameters, the data were graphed to synchronize subjects to their last dose. Results obtained from 001 and 002 clinical trials are shown in FIGS. 1–7.

FIG. 1 shows mean plots of white blood cell (WBC) counts of healthy volunteers receiving dosages 0 mg, 5 mg and 25 mg of rifalazil administered daily. Normal range of white blood cell counts, shown in the FIG. 1 as "L" and "H" lines, is between 4.5 and 11 K/CU MM. As seen in FIG. 1, the onset of decreases in the mean concentration of WBCs in both groups appeared about 4 days after beginning of dosing at day –8, reaching the nadir about 1 to 2 days after the last dose. The WBC counts decreased well below normal range of 4.5 K/CU MM.

Figure 2:
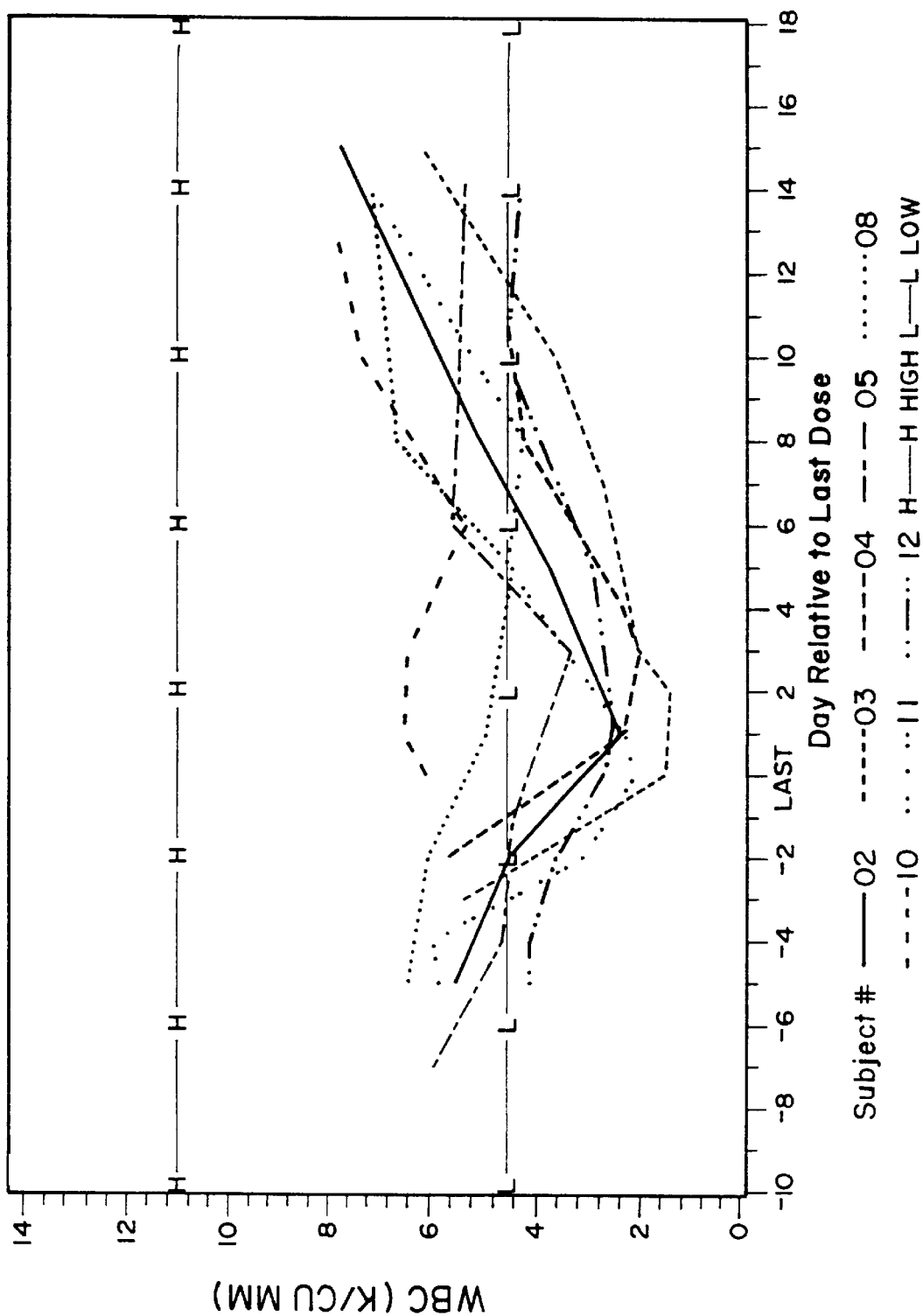
FIG. 2 illustrates decrease in white blood cells count in daily dosing regimen used in a clinical trial on human volunteers wherein the daily dose of rifalazil was 25 mg.

FIG. 2 shows individual white blood cell counts in healthy volunteers (Group 1) receiving 25 mg of rifalazil daily for 14 days. As seen in FIG. 2, subjects in Group 1 experienced a larger drop in WBC counts, however, only one subject had the WBC counts that fell below $2.0 \times 10^3/mm^3$, thle level which is approaching unsafe level.

Figure 3:
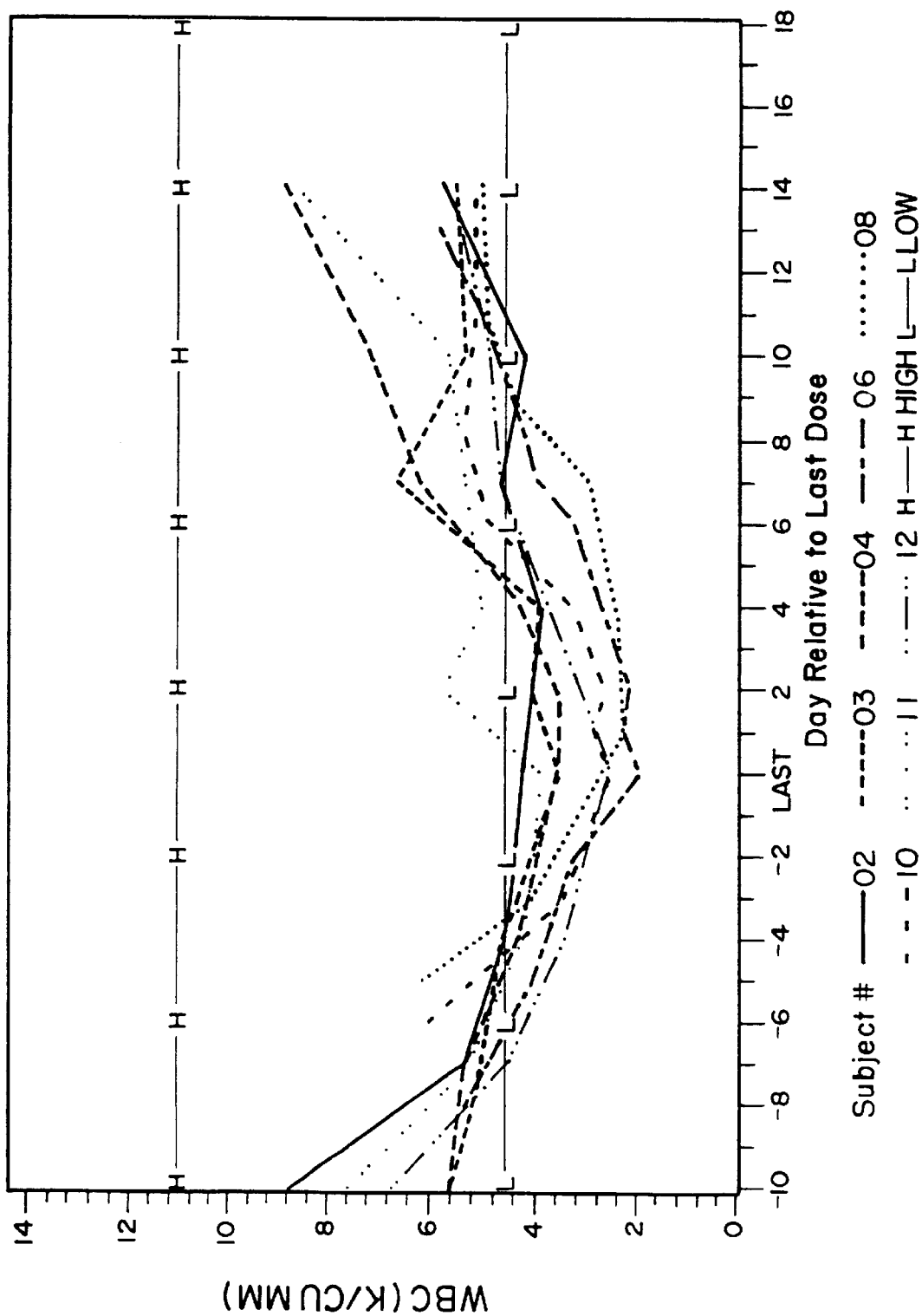
FIG. 3 illustrates decrease in white blood cells count in daily dosing regimen used in a clinical trial on human volunteers wherein the daily dose of rifalazil was 5 mg.

FIG. 3 shows individual white blood cell counts in healthy volunteers (Group 2) receiving 5 mg of rifalazil daily for 14 days. As seen in FIG. 3, subjects in Group 2 experienced lower decreases in WBC counts which agrees with findings that the number and severity of adverse reaction are dose-dependent.

Figure 4:
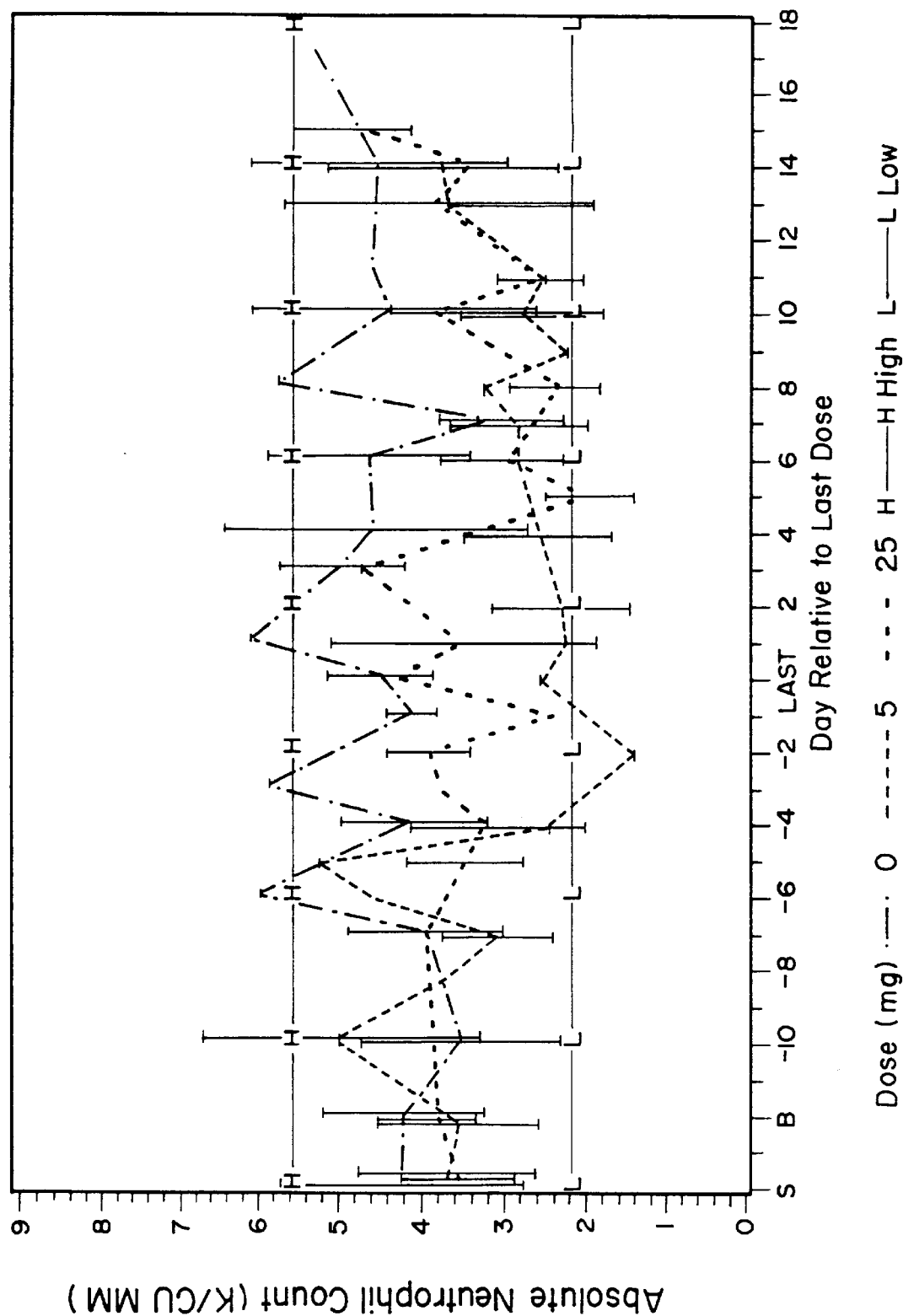
FIG. 4 illustrates changes in absolute neutrophil count in daily dosing regimen used in a clinical trial on human volunteers where the daily dose was 5 or 25 mg compared to a control group which received placebo without rifalazil.

FIG. 4 shows mean absolute neutrophil count in twenty-four healthy volunteers following administration of 0 mg, 5 mg and 25 mg of rifalazil daily for 14 days. As seen in FIG. 4, the absolute neutrophil count results have shown less consistent patterns making it difficult to establish the true nadir for each group.

Figure 5:
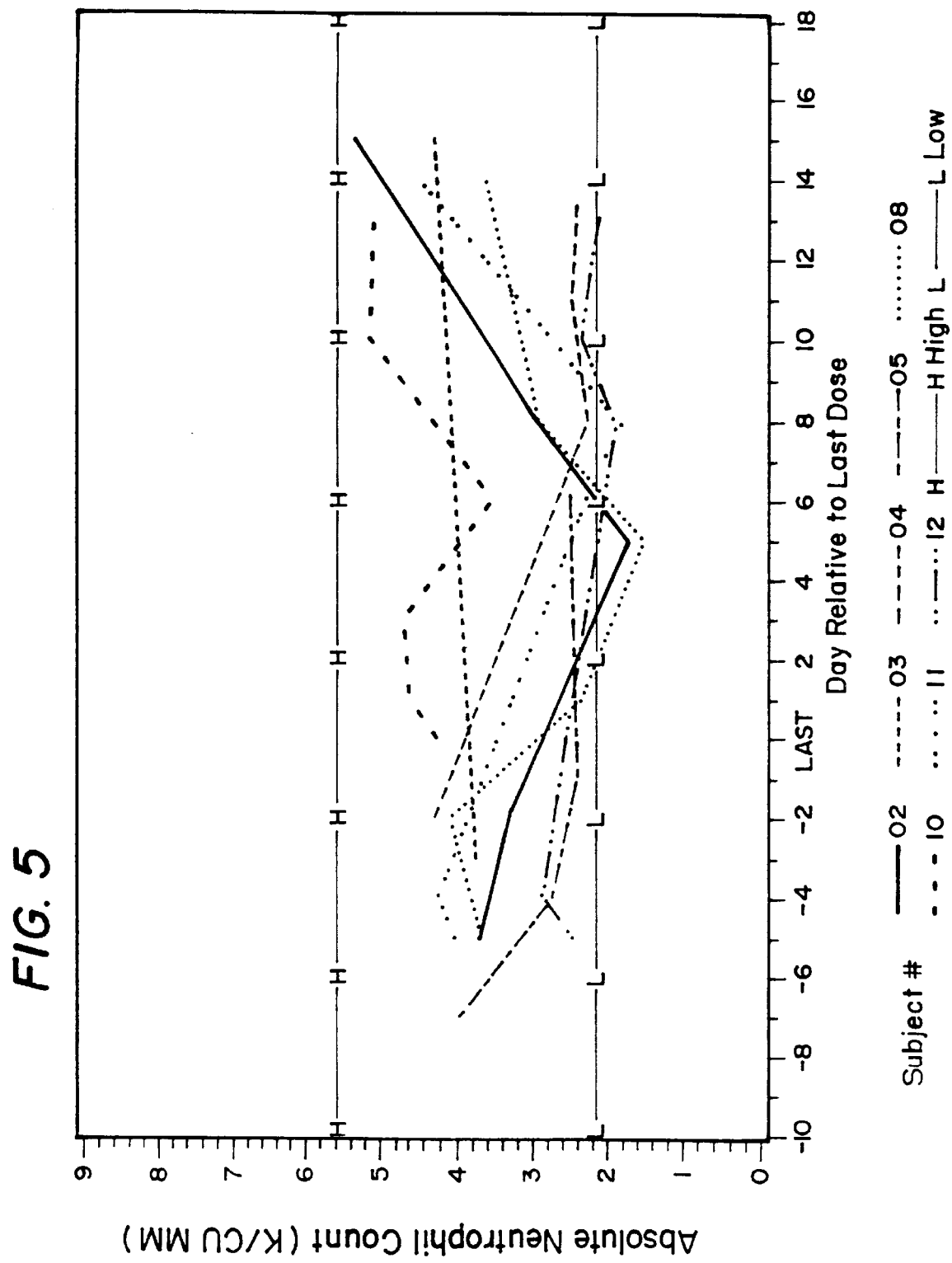
FIG. 5 illustrates decrease in absolute neutrophil count in daily dosing regimen used in a clinical trial on human volunteers wherein daily dose of rifalazil was 25 mg.
Figure 6:
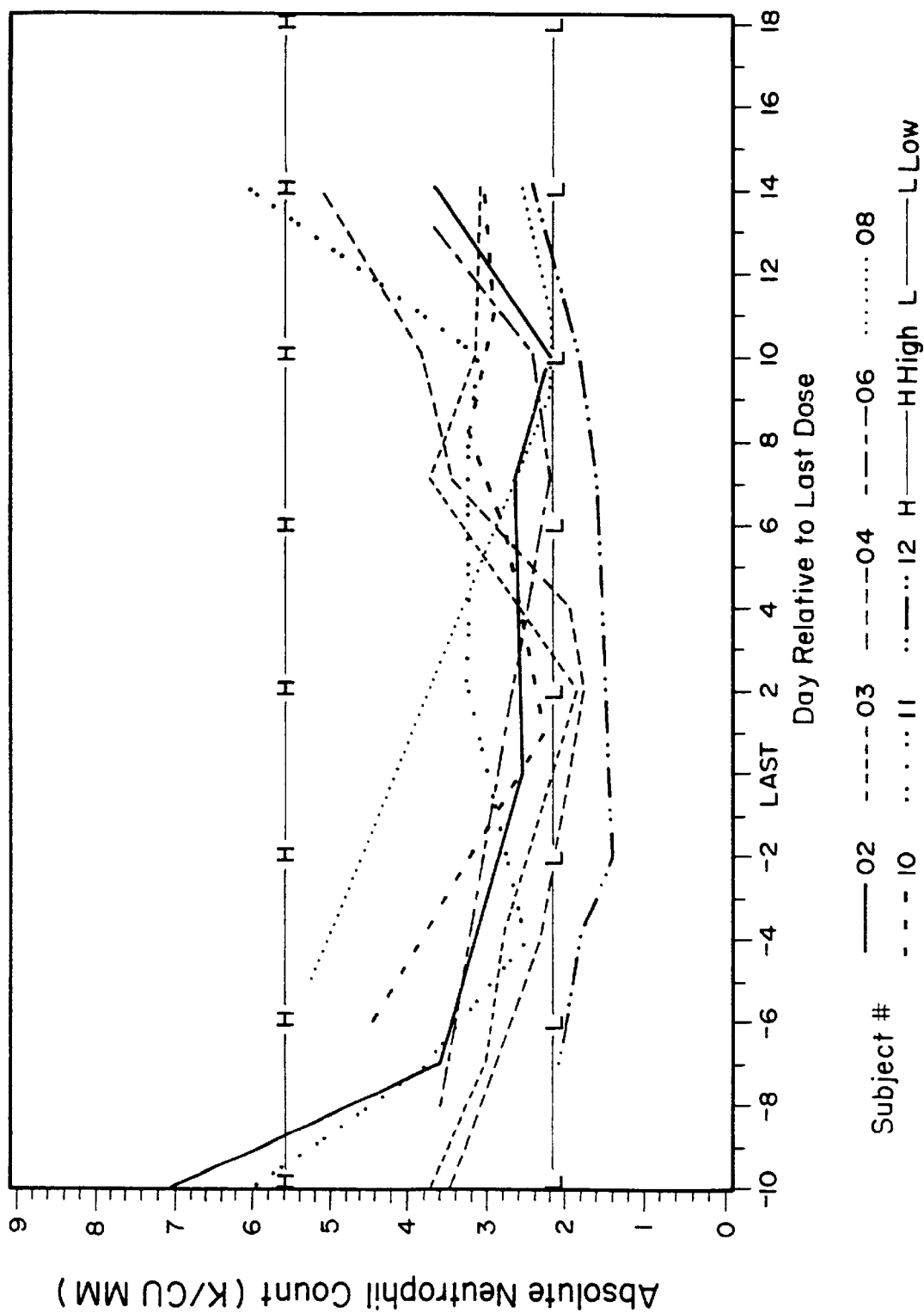
FIG. 6 illustrates decrease in absolute neutrophil count in daily dosing regimen used in a clinical trial on, human volunteers wherein daily dose of rifalazil was 5 mg.

FIGS. 5 and 6 show individual absolute neutrophil counts in Group 1 receiving 25 mg of rifalazil daily for 14 days and Group 2 receiving 5 mg rifalazil daily for 14 days, respectively. Four subjects in Group 1, receiving 25 mg of rifalazil, seen in FIG. 5, and 3 subjects in Group 2, receiving 5 mg of rifalazil, seen in FIG. 6, experienced ANC values $<2.0 \times 10^3/mm^3$, however no ANC value fell below $<1.0 \times 10^3/mm^3$ for any individual subject.

Figure 7:
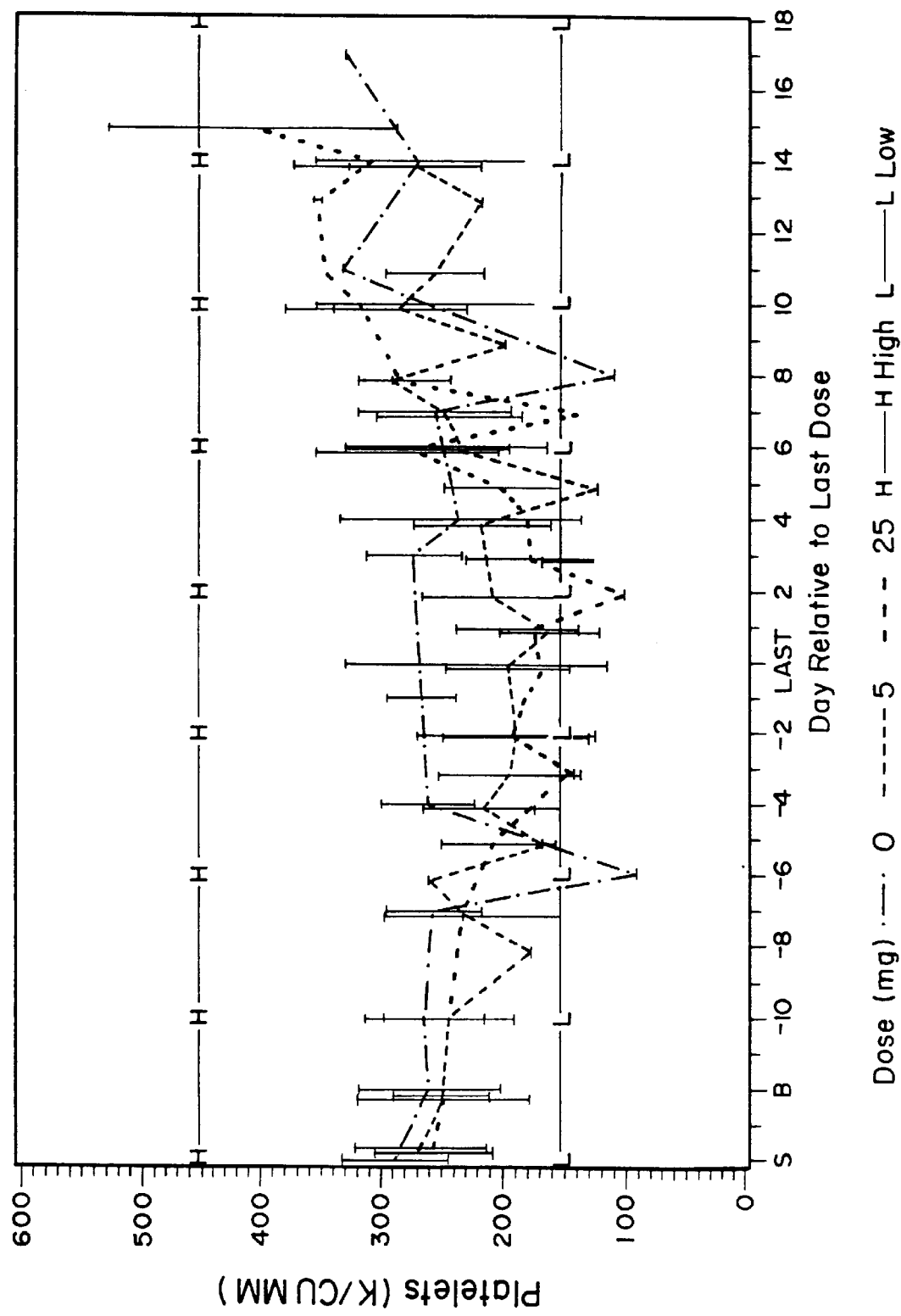
FIG. 7 illustrates changes in platelets counts after 20 daily administration of 5 and 25 mg rifalazil to healthy volunteers in a clinical trial compared to a control group receiving placebo.

Platelet counts, shown in FIG. 7, demonstrated small changes relative to placebo, with fewer changes occurring in the group receiving 5 mg of rifalazil versus the group receiving 25 mg. All hematologic parameters returned to normal within 14 days following administration of the last dose.

Figure 8:
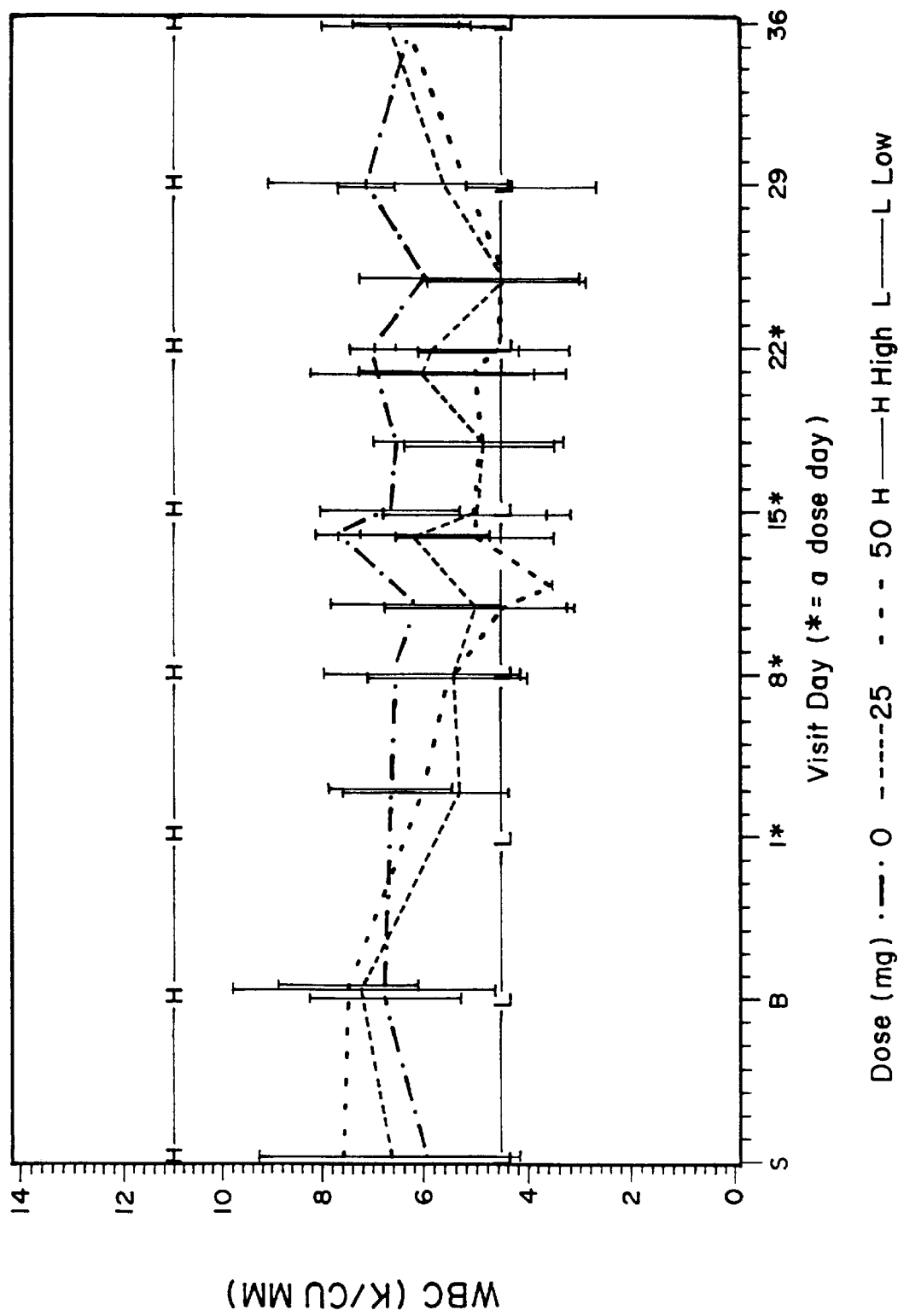
FIG. 8 illustrates changes in white blood cells after administration of once a week dose of 25 or 50 mg for five weeks to healthy volunteers in a clinical trial compared to a control group receiving placebo.
Figure 9:
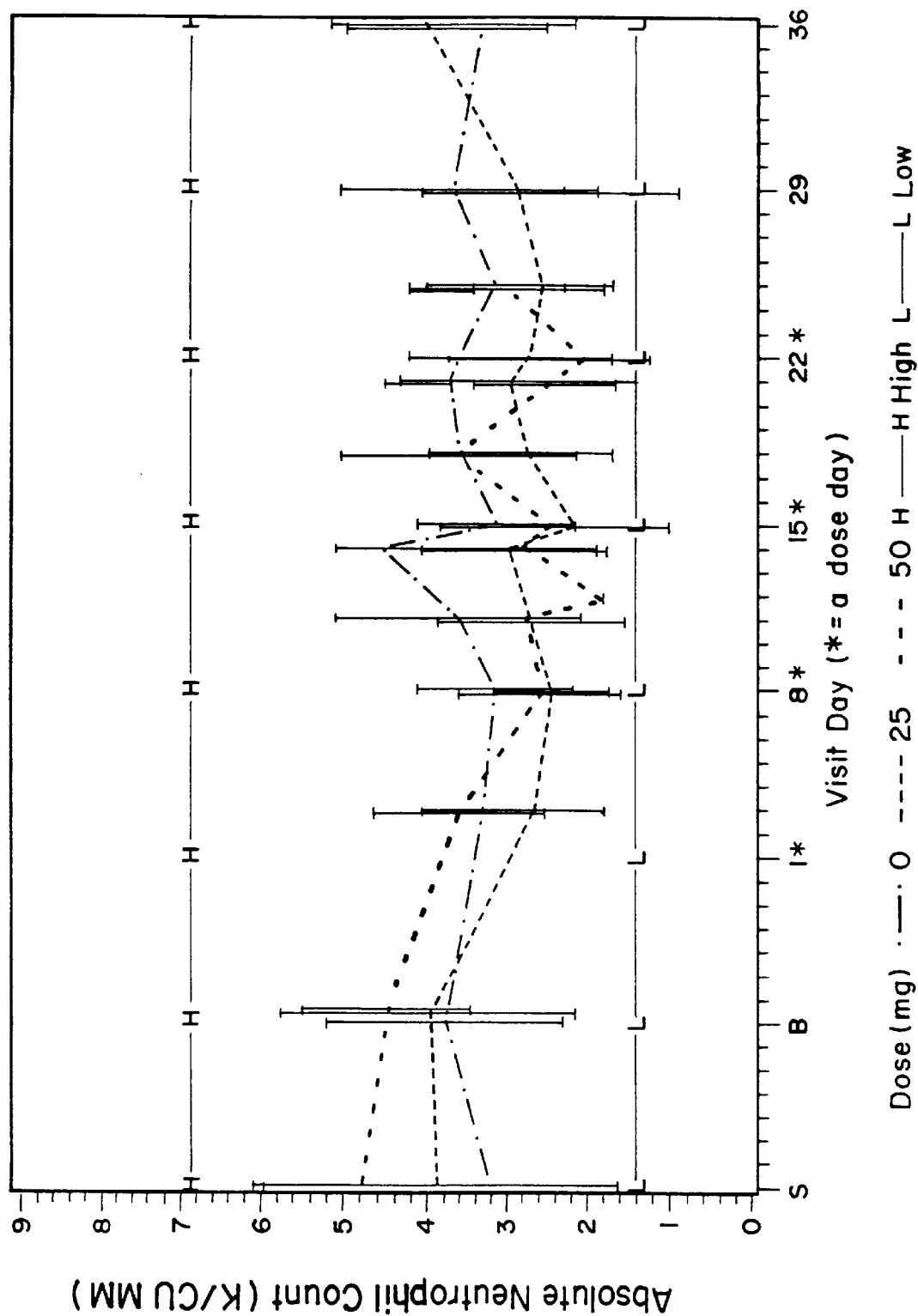
FIG. 9 illustrates changes in absolute neutrophil count after administration of once a week dose of 25 or 50 mg for five weeks to healthy volunteers in a clinical trials compared to a control group receiving placebo.
Figure 10:
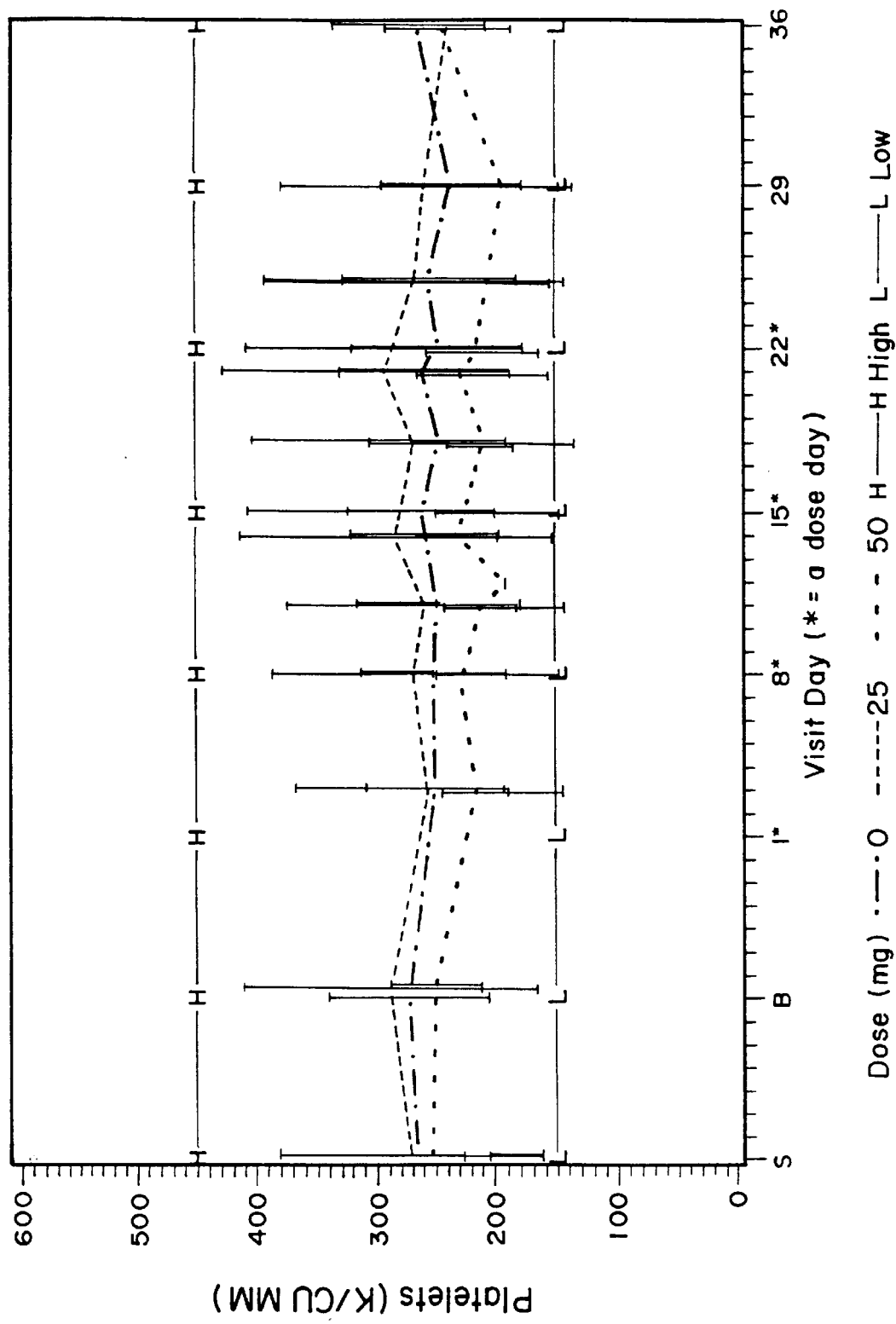
FIG. 10 illustrates changes in platelet count after administration of once a week dose of 25 or 50 mg for five weeks to healthy volunteers in a clinical trial compared to a control group receiving solely a placebo.

Results obtained in 004 clinical trial where the healthy volunteers received only one dose a week for four weeks are seen in FIGS. 8–10. Consistent with prior observations in 001 and 002 clinical trials, overall, this study resulted in changes of hematologic parameters of much smaller magnitude compared to the daily multiple-dose clinical trial 003.

FIG. 8 shows mean white blood cell plots for once a week dosage of 0 mg (control), 25 mg and 50 mg of rifalazil for four weeks. The subjects' hematological parameters were followed for an additional two weeks up to day 36.

When the results seen in FIG. 8 (once-a-week administration of 50 and 25 mg rifalazil) are compared to results seen in FIG. 1 (once-a-day administration of 5 and 25 mg of rifalazil), the differences in WBC counts are readily observed. In FIG. 1, both 50 and 25 dosages show continuous drop in WBC counts to around 2.0 K/CU MM. In FIG. 8, on the other hand, WBC counts stayed overall within the normal range between 4.5 and 11.0 K/CU MM.

FIG. 9 shows mean absolute neutrophil counts for once-a-week dosage of 0 mg (control), 25 mg and 50 mg of rifalazil administered for four weeks. As above, subjects ANC were followed up to day 36. Three subjects in the 25 mg group and four subjects in the 50 mg group had shown decreases in the ANC to below $2.0 \times 10^3/mm^3$ (data not shown). However, no subject experienced a drop in ANC below $1.0 \times 10^3/mm^3$ which is considered unsafe.

FIG. 10 shows mean platelet plots for once-a-week dosage of 0 mg (control), 25 mg and 50 mg of rifalazil for four weeks with follow up to day 36. As seen in FIG. 10, once a week dosages of rifalazil on platelets were unremarkable without any observable changes outside of the normal range 150–450 K/CU MM.

All hematologic parameters returned to normal by 14 days, after administration of the last dose.

Pharmacokinetic analyses associated with clinical trials involved measurement of concentrations of rifalazil in plasma and/or whole blood of subjects participating in the four Phase 1 studies using high performance liquid chromatography. Most pharmacokinetic parameters derived in these studies are reflective of different dosing schedules, and conditions, such as fasted or fed subjects, and thus are not directly comparable across studies.

Results are shown in Table 7 for the 001 and 002 clinical trials, in Table 14 for the 003 clinical trial and in Table 15 for the 004 clinical trial 004. Several pharmacokinetic patterns were consistently observed. Rifalazil appears to be slowly absorbed, widely distributed, and slowly eliminated via a multi-phasic process. Inter-patient variability was demonstrated.

Due to extremely low levels of rifalazil measured in the urine, elimination of rifalazil seems to be non-renal, and probably occurs by the fecal route. In addition, low levels of oxidative metabolites of rifalazil were found in plasma. This further suggests that drug is excreted in the feces either in unchanged form or as conjugates of the parent drug.

Attempts were made to analyze the multiple-dose pharmacokinetics using a linear 3-compartment model, and a 3-compartment model incorporating enzyme induction. However, neither multi-compartmental model accurately characterized the pharmacokinetic parameters in all subjects. Daily dosing and related early terminations due to adverse reactions, differences in bioavailability from a food effect, and nonconnective dose administration further complicated these analyses. Therefore, only noncompartmental pharmacokinetic parameters were derived for clinical trials 003 and 004.

TABLE 14

Pharmacokinetics Parameters in 003 Clinical Trial

| Parameters (mean) | Group 2 5 mg/day First Dose | Group 2 5 mg/day Last Dose (day 14) | Group 1 25 mg/day First Dose |
|---|---|---|---|
| Tmax (h) | 5.25 | 4.57 | 5.62 |
| Cmax (ng/mL) | 13.3 | 13.41 | 41.26 |
| Half-Life (h) | | | |
| distribution $t_{1/2}$ | 10.07 | 17.26 | 12.5 |
| elimination $t_{1/2}$ | — | — | |
| AUC (ng.h/mL) | | | |
| 0–24 | 137 | 187 | 479 |
| 0–∞ | 178 | — | 688 |

TABLE 14-continued

Pharmacokinetics Parameters in 003 Clinical Trial

[1]Steady-state noncompartmental pharmacokinetics could not be assessed in Group 1 due to early terminations and missed doses.

Table 14 shows noncompartmental pharmacokinetics parameters derived from daily dosing for up to 14 days in 003 clinical trial.

For the 004 clinical trial, the pharmacokinetic analysis of this multiple-dose study was limited to a comparison of the noncompartmental parameters obtained from the first dose (Day 1) data versus the fourth (last) dose (Day 22). Because of extensive sampling after the fourth dose, this study yielded the most complete data about terminal elimination of rifalazil given in a multiple-dose regimen. Results are shown in Table 15.

TABLE 15

Pharmacokinetic Parameters in 004 Clinical Trial

| Parameters (mean) | Dose | | | |
|---|---|---|---|---|
| | 25 mg/wk First Dose | 25 mg/wk Last Dose | 50 mg/wk First Dose | 50 mg/wk Last Dose |
| Tmax (h) | 5.7 | 5.7 | 5.5 | 6.0 |
| Cmax (ng/mL) | 39.3 | 43.8 | 69.78 | 79.1 |
| Half-Life (h) | | | | |
| distribution $t_{1/2}$ | 10.5 | 11.3 | 9.5 | 12.0 |
| elimination $t_{1/2}$ | — | 60.9 | — | 109.1 |
| AUC (ng.h/mL) | | | | |
| 0–24 | 472.2 | 552.6 | 795.3 | 1013.0 |
| 0–∞ | 628.7 | 1347.3 | 1019.1 | 2840.6 |

As shown in Table 15, $C_{max}$ and AUC values demonstrate dose-proportionate increases. The $C_{max}$ from the fourth dose (Day 22) was about 44 ng/mL in the 25 mg dose group, and about 79 ng/mL in the 50 mg group. The change between values on Day 1 and Day 22 was not statistically significant. The mean apparent terminal half-life was approximately 61 hours after the 25 mg dose, and about 110 hours after the 50 mg dose, although the range was quite variable (29.5 to 106.8 hours and 65.9 to 148 hours, respectively). The $AUC_{(0-24)}$ increased on Day 22 approximately 17% for the 25 mg dose and 27% for the 50 mg dose, relative to Day 1 AUC values. Similar noncompartmental pharmacokinetic parameters were demonstrated after 25 mg doses in both 003 and 004 clinical trials.

4. Summary and Conclusions of Phase I Clinical Trials 001–004

The four Phase I clinical trials have investigated the safety profile and pharmacokinetics in healthy male subjects following the administration of rifalazil as single doses (300 mg, 100 mg, 30 mg), daily doses (25 mg, 5 mg) administered for 14 days, and weekly doses (50 mg, 25 mg) administered for 4 weeks. Results demonstrated a clear dose-related incidence in the number and severity of adverse reactions. The predominate adverse reactions comprised "flu-like" symptoms, which are also known to be present with rifampin and rifabutin, other agents in the same pharmacologic class. The symptoms are generally mild, and rarely resulted in discontinuation of drug at lower and less frequent dosing regimens. For daily dosing regimen, however, the symptoms became more pronounced and several patients discontinued the study.

The changes in hematologic parameters also appeared to be dose-related. Although decreases in WBC and ANC values to less than the normal ranges occurred, they returned to normal levels within two weeks of dose completion. Increasing the dosing interval by changing the administration from once daily to once weekly diminished both the number and severity of adverse reactions and also the decreases in hematologic parameters. In terms of frequency and severity, a dose of 25 mg or 50 mg given weekly in healthy subjects yielded a tolerable safety profile.

Pharmacokinetic analysis has clearly demonstrated that the administration of food with rifalazil delayed absorption and increased $C_{max}$ and AUC in a dose-proportional manner. The mean terminal half-life seen with the 25 mg dose was about 61 hours. Accumulation of rifalazil with either 25 mg or 50 mg doses, given once weekly over 4 weeks to healthy subjects, appeared to be minimal.

After administration of a dose of 25 mg, the average $C_{max}$ achieved was about 44 ng/mL, which was 2 to 3 times the $MIC_{90}$ of rifampin-sensitive *Mycobacterium tuberculosis* (15.6 ng/mL) Furthermore, because of the partitioning of rifalazil into macrophages, therapeutically beneficial concentrations of rifalazil are expected to persist in macrophages longer than in plasma. Thus, plasma concentrations that fall below the $MIC_{90}$ during the dosing interval may be clinically insignificant in disease treatment, because the drug may be stored in macrophages.

B. Efficacy of Rifalazil Treatment in TB Patients—Clinical Trial 005

Following the studies performed on healthy volunteers, clinical trial 005 was initiated for treatment of tuberculosis patients with isoniazid (INH) alone administered daily, or isoniazid combined with rifampin both administered daily, or isoniazid administered daily with either 10 mg or 25 mg of rifalazil administered weekly.

Dosages of isoniazid and rifampin were adjusted to body weight of patients. When the patient's body weight was less than 35 kg, isoniazid was administered in 10 mg/kg/dose with maximum dose 300 mg, and rifampin was administered in 10 mg/kg/dose with maximum dose of 450 mg/dose. When the patient's body weight was between 35 and 45 kg, isoniazid was administered in 300 mg/dose and rifampin in 450 mg/dose. When the patient's body weight was greater than 45 kg, isoniazid was administered as 600 mg/dose.

In these studies, the following tests were performed and are presented in Tables 16–21. Change in $Log_{10}$ of colony forming units (CFU) per mL of sputum of microbiologically evaluable patients is shown in Table 16. WBC, ANC and platelets counts in INH treated patients, is shown in Table 17. WBC, ANC and platelet counts in patients treated with INH and rifampin, are shown in Table 18. WBC, ANC and platelet counts in patients treated with INH daily and 10/25 mg of rifalazil weekly, are shown in Tables 19 and 20, respectively. Rifalazil concentration in patients treated with INH and 10 or 25 mg of rifalazil, are shown in Table 21. Definite diagnosis and evaluation of treatment efficacy requires direct examination of sputum for the presence of *M. tuberculosis*. The extent of *M. tuberculosis* infection is determined by number of bacteria able to form colonies and is expressed as colony forming units. When the number of colony forming units (CFU) is high, the infection is unhindered. When the CFU decreases, the number of active *M. tuberculosis* bacteria decreases. The CFU, typically expressed as $Log_{10}$, have therefore important diagnostic and treatment evaluative value.

One challenge to evaluating the effectiveness of new diagnostics and treatment for tuberculosis is the long time interval required for measuring decreases in CFU levels and observable clinical improvements. That is to say, the treatment of tuberculosis is of long duration (typically at least 6 months) and as a consequence only after several months of therapy is it possible to determine if clinical benefit is achieved. Therefore, clinical studies have been designated to evaluate the early bactericidal activity (EBA) of new tuberculosis therapies. The EBA of a therapy can be defined as the activity observed during the initial phase (e.g., initial 1–2 weeks) of treatment. Clinical studies that incorporate EBA analyses are based on the contention that EBA is a good index of ultimate therapeutic benefit that is observed several months later.

Table 16 which shows sputum baseline to day 15 in $Log_{10}$ CFU/mL of sputum microbiologically evaluable patients compares the reduction in colony forming units (CFU) for the four different groups of patients over the first two weeks of the therapy. The four groups of patients were treated as follows: Group 1 received INH daily for 14 days, Group 2 received INH daily plus rifampin daily for 14 days, Group 3 received INH daily for 14 days plus rifalazil once per week (10 mg on day 1 and day 8) over 14 days, and Group 4 received INH daily for 14 days plus rifalazil once per week (25 mg on day 1 and day 8) over 14 days. Dosages of isoniazid and rifampin depended on the patient's weight and were as above. The number of patients in each study group are presented as the N value.

The number of patients in Groups 1–4, was six, four, six, and six, respectively. The mean change in sputum CFU following these treatments is also shown. The change in CFUs is greatest for Groups 2 and 4 which received daily treatment with INH in combination with rifampin administered daily (Group 2) or INH administered daily in combination with rifalazil administered once-a-week at 25 mg dosages (Group 4). These data show that rifalazil administered weekly or twice weekly in relatively very low dosages of 10 or 25 mg is an effective substitute for rifampin (600 mg/day administered daily) in the routine therapy for tuberculosis.

TABLE 16

Change from Sputum Baseline to Day 15 in $Log_{10}$ CFU/mL of Sputum Microbiologically Valuable Patients

| $Log_{10}$ CFU/mL | INH 400 mg | INH + RMP 400 mg + 600 mg | INH + Rifalazil 400 mg + 10 mg | INH + Rifalazil 400 mg + 25 mg |
|---|---|---|---|---|
| N | 6 | 4 | 6 | 6 |
| Mean (SD) | −1.58 (0.51) | −2.61 (0.94) | −2.22 (0.98) | 2.74 (0.73) |
| Med | −1.63 | −2.84 | −2.25 | −2.78 |
| Min | −2.28 | −3.41 | −3.24 | −3.67 |
| Max | −0.92 | −1.34 | −0.65 | −1.55 |

These results clearly show that administration of INH-rifalazil once-a-week in 10 or particularly 25 mg doses is as efficacious treatment for tuberculosis as treatment with INH-rifampin daily.

The four tables 17–20 show hematology data which are separated according to Groups 1–4. The group treatment corresponds to those seen in Table 16. These data provide safety information regarding the adverse reactions because hematologic perturbations are considered to be among the most clinically important adverse reactions associated with treatment by rifamycin type drugs. In particular, the ANC value is considered to be a very meaningful safety index as it directly relates to a patient's ability to fight infection.

As seen in Tables 17–20, in the upper section, white blood cell counts decreased slightly after the baseline values in all groups during the treatment but did not reach critically low levels. Once a week treatment with 10 mg rifalazil combined with 400 mg or less of INH administered daily did not lead to decrease in WBC.

Upon comparison of the ANC values for Groups 1, 2, 3 and 4 (Tables 17–20) a drop in ANC was observed after the baseline values for groups 2–4. A lower ANC value, however, is not of great concern, however, until it drops below 1.0 K/CU MM. That level was reached in only one patient in Group 3, treated with INH plus rifalazil at 10 mg but that patient had a low ANC value to begin with.

Platelet levels were not affected by any treatment and were, therefore, not safety concern.

The important conclusions derived from the hematologic data is that rifalazil does not cause a greater level of hematologic disturbances (safety concerns) than rifampin which is routinely used for treatment of TB. Rifalazil is therefore as safe as rifampin and as efficacious in lower and less frequent dosages.

TABLE 17

WBC, ANC, and Platelet Counts (K/CU MM) - INH

|   | Baseline | Day 4 | Day 8 | Day 11 | Day 15 | Day 28 | Day 42 |
|---|---|---|---|---|---|---|---|
| n | 8 | 8 | 7 | 7 | 7 | 3 | 2 |
| WBC (K/CU UM) | | | | | | | |
| Mean (SD) | 8.90 (1.87) | 10.88 (6.87) | 9.08 (2.23) | 8.28 (0.97) | 9.23 (2.28) | 8.31 (2.48) | 7.98 (1.77) |
| Med | 8.55 | 8.81 | 8.63 | 8.10 | 8.49 | 7.06 | 7.98 |
| Min | 6.77 | 6.37 | 6.21 | 7.27 | 6.82 | 6.70 | 6.73 |
| Max | 11.60 | 27.19 | 12.06 | 10.03 | 12.40 | 11.16 | 9.23 |
| ANC (K/CU UM) | | | | | | | |
| Mean (SD) | 6.04 (1.92) | 7.62 (6.29) | 5.96 (2.05) | 5.29 (0.96) | 5.95 (2.08) | 5.63 (1.95) | 6.96 (0.34) |
| Med | 5.68 | 5.47 | 5.22 | 5.06 | 6.04 | 4.60 | 6.96 |
| Min | 3.90 | 3.79 | 3.34 | 4.17 | 3.51 | 4.41 | 6.72 |
| Max | 8.74 | 22.51 | 9.32 | 6.57 | 8.84 | 7.87 | 7.2 |
| Platelets (K/CU UM) | | | | | | | |
| Mean (SD) | 295.75 (93.28) | 309.38 (96.56) | 310.13 (91.03) | 336.10 (89.51) | 298.59 (84.98) | 287.27 (102.57) | 297.10 (67.74) |
| Med | 253.35 | 305.65 | 357.20 | 354.20 | 302.00 | 266.00 | 297.10 |
| Min | 227.10 | 153.70 | 185.60 | 208.10 | 184.60 | 197.00 | 249.20 |
| Max | 464.40 | 431.70 | 396.20 | 447.50 | 412.70 | 398.80 | 345.00 |

TABLE 18

WBC, ANC, and Platelet Counts (K/CU MM) INH + RMP

|   | Baseline | Day 4 | Day 8 | Day 11 | Day 15 | Day 28 | Day 42 |
|---|---|---|---|---|---|---|---|
| WBC (K/cu mm) | | | | | | | |
| n | 8 | 8 | 8 | 8 | 8 | 7 | 4 |
| Mean (SD) | 9.86 (3.47) | 8.22 (4.01) | 8.75 (5.16) | 8.28 (3.83) | 7.80 (4.36) | 8.19 (3.50) | 8.36 (5.61) |
| Med | 8.59 | 6.95 | 6.40 | 5.60 | 5.85 | 6.69 | 6.10 |
| Min | 6.76 | 4.08 | 4.71 | 5.27 | 4.27 | 4.90 | 4.67 |
| Max | 15.84 | 16.90 | 20.23 | 16.40 | 15.73 | 14.20 | 16.55 |
| ANC (K/cu mm) | | | | | | | |
| n | 8 | 8 | 8 | 8 | 8 | 7 | 4 |
| Mean (SD) | 6.71 (3.69) | 4.97 (4.37) | 5.45 (5.14) | 5.04 (4.26) | 4.53 (4.10) | 5.09 (3.83) | 5.50 (5.38) |
| Med | 5.21 | 3.33 | 3.26 | 3.22 | 2.74 | 3.44 | 3.82 |
| Min | 3.00 | 1.78 | 1.36 | 1.73 | 1.47 | 1.59 | 1.18 |
| Max | 13.37 | 14.69 | 16.98 | 14.26 | 12.42 | 11.41 | 13.18 |
| Platelets (K/cu mm) | | | | | | | |
| n | 8 | 8 | 8 | 8 | 8 | 6 | 3 |
| Mean (SD) | 363.16 (148.71) | 376.78 (217.40) | 429.23 (194.32) | 416.00 (190.23) | 365.20 (163.83) | 387.13 (287.01) | 427.90 (234.40) |

TABLE 18-continued

WBC, ANC, and Platelet Counts (K/CU MM) INH + RMP

|  | Baseline | Day 4 | Day 8 | Day 11 | Day 15 | Day 28 | Day 42 |
|---|---|---|---|---|---|---|---|
| Med | 336.80 | 320.00 | 358.30 | 372.45 | 300.30 | 245.80 | 490.00 |
| Min | 194.30 | 136.20 | 233.30 | 185.00 | 222.00 | 175.00 | 168.70 |
| Max | 580.30 | 785.00 | 746.00 | 750.00 | 671.60 | 874.70 | 625.00 |

TABLE 19

WBC, ANC, and Platelet Counts (K/CU MM) - INH + 10 mg-Rifalazil

|  | Baseline | Day 4 | Day 8 | Day 11 | Day 15 | Day 28 | Day 42 |
|---|---|---|---|---|---|---|---|
| WBC (K/cu mm) | | | | | | | |
| n | 8 | 8 | 8 | 8 | 8 | 4 | 3 |
| Mean (SD) | 7.97 (1.41) | 7.85 (2.66) | 8.36 (3.43) | 7.96 (2.78) | 8.22 (2.60) | 6.05 (2.69) | 5.87 (1.18) |
| Med | 7.73 | 7.90 | 8.61 | 8.20 | 7.95 | 5.82 | 5.98 |
| Min | 6.59 | 5.20 | 4.47 | 3.75 | 4.61 | 3.01 | 4.64 |
| Max | 11.24 | 13.41 | 15.07 | 12.29 | 12.09 | 9.57 | 7.00 |
| ANC (K/cu mm) | | | | | | | |
| n | 8 | 8 | 8 | 8 | 8 | 4 | 3 |
| Mean (SD) | 4.91 (1.13) | 4.61 (1.95) | 4.98 (2.57) | 4.71 (2.34) | 4.51 (2.46) | 3.27 (1.73) | 3.08 (1.33) |
| Med | 4.94 | 4.10 | 5.09 | 4.76 | 4.22 | 3.53 | 2.65 |
| Min | 3.33 | 2.60 | 1.67 | 1.46 | 1.42 | 0.93 | 2.02 |
| Max | 6.70 | 7.99 | 8.86 | 7.80 | 7.89 | 5.09 | 4.58 |
| Platelets (K/cu mm) | | | | | | | |
| n | 8 | 8 | 8 | 8 | 8 | 3 | 2 |
| Mean (SD) | 358.01 (98.58) | 391.89 (100.83) | 403.21 (104.39) | 358.35 (95.30) | 344.36 (53.48) | 335.67 (94.42) | 262.30 (48.55) |
| Med | 333.25 | 377.60 | 408.65 | 376.90 | 341.30 | 300.10 | 262.30 |
| Min | 293.00 | 277.7 | 273.10 | 222.20 | 271.00 | 264.20 | 227.90 |
| Max | 590.00 | 577.30 | 569.00 | 463.00 | 426.40 | 442.70 | 296.70 |

TABLE 20

WBC, ANC, and Platelet Counts (K/CU MM) INH + 25 mg-Rifalazil

|  | Baseline | Day 4 | Day 8 | Day 11 | Day 15 | Day 28 | Day 42 |
|---|---|---|---|---|---|---|---|
| WBC (K/cu mm) | | | | | | | |
| n | 7 | 7 | 7 | 7 | 7 | 3 | 2 |
| Mean (SD) | 11.67 (6.27) | 10.49 (6.79) | 11.76 (7.15) | 8.76 (4.86) | 8.86 (4.49) | 9.64 (5.59) | 11.59 (6.19) |
| Med | 10.37 | 8.05 | 10.24 | 7.42 | 7.62 | 9.43 | 11.59 |
| Min | 6.46 | 4.63 | 4.08 | 3.70 | 3.62 | 4.16 | 7.21 |
| Max | 24.23 | 22.69 | 21.68 | 17.23 | 15.79 | 15.33 | 15.97 |
| ANC (K/cu mm) | | | | | | | |
| n | 7 | 7 | 7 | 7 | 7 | 3 | 2 |
| Mean (SD) | 8.52 (5.17) | 7.07 (6.52) | 8.90 (6.45) | 5.91 (4.42) | 5.97 (3.84) | 6.01 (3.64) | 7.39 (3.77) |
| Med | 6.62 | 4.05 | 7.78 | 4.40 | 5.17 | 6.70 | 7.39 |
| Min | 4.01 | 2.85 | 2.28 | 2.03 | 1.70 | 2.07 | 4.72 |
| Max | 18.70 | 17.06 | 18.69 | 14.57 | 12.81 | 9.25 | 10.05 |
| Platelets (K/cu mm) | | | | | | | |
| n | 7 | 7 | 7 | 7 | 7 | 4 | 3 |

TABLE 20-continued

WBC, ANC, and Platelet Counts (K/CU MM)
INH + 25 mg-Rifalazil

|  | Baseline | Day 4 | Day 8 | Day 11 | Day 15 | Day 28 | Day 42 |
|---|---|---|---|---|---|---|---|
| Mean (SD) | 395.03 (244.00) | 273.60 (143.15) | 426.57 (258.92) | 416.89 (248.05) | 373.04 (146.65) | 307.63 (141.68) | 251.37 (147.00) |
| Med | 319.60 | 222.80 | 407.50 | 461.20 | 410.90 | 314.10 | 185.40 |
| Min | 159.10 | 117.00 | 165.80 | 141.00 | 154.50 | 136.50 | 148.90 |
| Max | 846.20 | 483.30 | 930.00 | 884.90 | 547.00 | 485.80 | 419.80 |

Table 21 summarizes the plasma concentrations data of rifalazil measured in patients that received rifalazil at zero hour. The data are separated into 2 groups and are identified as INH+10 mg rifalazil (Group 3) and INH+25 mg rifalazil (Group 4). The concentration of rifalazil in plasma is presented in ng/mL and are shown as a timecourse (hours and days) wherein values were determined at several times over the two weeks of the study.

Typical daily dose of rifampin >600 mg given daily has resulted in the following adverse reactions including "flu-like" symptoms, such as fever, headaches, chills, malaise and other reactions listed above in hematopoietic reactions, such as leukopenia, thrombocytopenia, acute hemolytic anemia, and in cutaneous, gastrointestinal (GI) and hepatic reactions, shortness of breath, shock and renal failure.

TABLE 21

Rifalazil Concentration in Plasma (ng/mL)

| Treatment Group | Hour | | | | | | | | Day 8 | Day 8 | | |
|---|---|---|---|---|---|---|---|---|---|---|---|---|
|  | 0 | 3 | 6 | 9 | 12 | 24 | 48 | 72 | H-0 | H-6 | Day 11 | Day 15 |
| INH + 10 mg KRM | | | | | | | | | | | | |
| n | 4 | 4 | 4 | 4 | 4 | 4 | 2 | 3 | 3 | 4 | 2 | 3 |
| Mean | 0 | 9.7 | 12.58 | 9.95 | 10.7 | 3.6 | 2.5 | 1.4 | 0 | 16.83 | 2.4 | 0 |
| (SD) | (0) | (9.97) | (7.92) | (8.50) | (1.68) | (1.12) | (0.42) | (1.22) | (0) | (5.04) | (0.57) | (0) |
| Med | 0 | 9.0 | 11.9 | 10.3 | 11.4 | 3.55 | 2.5 | 2.0 | 0 | 18.0 | 2.4 | 0 |
| Min | 0 | 0 | 4.2 | 0 | 6.2 | 2.3 | 2.2 | 0 | 0 | 9.7 | 2.0 | 0 |
| Max | 0 | 20.8 | 72.7 | 19.2 | 11.6 | 5.0 | 2.8 | 2.2 | 0 | 21.5 | 2.3 | 0 |
| INH + 25 mg KRM | | | | | | | | | | | | |
| n | 6 | 6 | 6 | 6 | 6 | 6 | 5 | 4 | 5 | 6 | 6 | 4 |
| Mean | 0 | 15.93 | 28.47 | 21.62 | 16.83 | 7.72 | 3.48 | 2.15 | 0 | 29.02 | 4.12 | 0.85 |
| (SD) | (0) | (13.90) | (12.53) | (10.34) | (4.16) | (3.03) | (2.12) | (1.47) | (0) | (12.01) | (2.48) | (1.7) |
| Med | 0 | 11.4 | 30.85 | 22.15 | 18.1 | 6.7 | 3.9 | 2.7 | 0 | 28.5 | 3.0 | 0 |
| Min | 0 | 2.8 | 5.5 | 9.2 | 11.1 | 4.3 | 0 | 0 | 0 | 11.7 | 2.2 | 0 |
| Max | 0 | 38.4 | 42.7 | 38.2 | 20.6 | 12.2 | 5.3 | 3.2 | 0 | 43.0 | 6.3 | 3.4 |

The observed plasma levels of rifalazil were similar to those seen in normal volunteers. Table 21 shows that the plasma concentration of rifalazil increases from the zero level to 9.7 ng/mL for 10 mg of rifalazil and to 15.93 ng/mL in three hours showing a maximum concentration of the drug in plasma at six hours following the drug administration (12.68 ng/mL for 10 mg rifalazil and 28.47 ng/mL for 25 mg rifalazil). The drug concentration in plasma slowly decreases but there is still measurable amount of drug in plasma at 72 hours (3 days). After the second administration at day 8, the drug concentrations in both groups were found to be higher than following the first administration.

The data obtained in TB patients show that rifalazil administered once or twice weekly is effective for treatment of tuberculosis and has lesser adverse reactions than other currently available treatments. Additionally, these data once again illustrate the unexpected difference between human and animal pharmacokinetic data.

C. Comparison of Rifalazil Treatment with Rifampin and Rifabutin

When similar studies with two other currently FDA approved rifamycins, rifampin and rifabutin were made, the following adverse reactions were observed with typical daily dose of rifampin and rifabutin.

GI reactions included heartburn, epigastric distress, anorexia, nausea, vomiting, gas, cramps, diarrhea, sore mouth and tongue, pseudomembranous colitis, pancreatitis, and were experienced by 1% to 2% subjects.

Hepatic reactions included asymptomatic elevations of liver enzymes (up to 14%) and hepatitis (<1%). Other reactions such as shock-like syndrome with hepatic involvement were present but rare. Abnormal liver function tests, transient abnormalities in liver function tests, such as elevations in serum bilirubin, BSP, alkaline phosphatase, serum transaminase were also observed.

Dermatologic reactions included rash observed in 1% to 5% of subjects, pruritus, urticaria, pemphigoid reaction, flushing.

CNS reactions included headache, drowsiness, fatigue, dizziness, inability to concentrate, mental confusion, generalized numbness, behavioral changes, and, rarely, also ocular myopathy.

Hematologic reactions included eosinophilia, transient leukopenia, hemolytic anemia, decreased hemoglobin, hemolysis and thrombocytopenia.

Musculoskeletal reactions included ataxia, muscular weakness, pain in extremities, osteomalacia and myopathy.

Opthalmologic reactions included visual disturbances and exudative conjunctivitis.

Renal reactions included hemoglobinuria, hematuria; renal insufficiency and acute renal failure.

Miscellaneous other adverse reactions associated with rifampin included menstrual disturbances, fever, elevation in BUN and elevated serum uric acid, possible immunosuppression, isolated reports of abnormal growth of lung tumors, reduced 25-hydroxycholecalciferol levels, edema of face and extremities, shortness of breath, wheezing, decrease in blood pressure and shock.

Rifabutin (150–300 mg single dose) also causes adverse reactions although it is generally better tolerated than rifampin. Discontinuation of therapy due to an adverse event was required in 16% of patients receiving rifabutin vs. 8% with placebo. Primary reasons for discontinuation were rash adverse reactions included flu-like symptoms, hepatitis, hemolysis, arthralgia, myositis, chest pressure or pain with dyspnea, skin discoloration (<1%), seizure, paraesthesia, aphasia, confusion, and non-specific T wave changes on ECG. When rifabutin was administered at doses from 1050 to 2400 mg/day, generalized arthralgia and uveitis occurred. These experiences abated when rifabutin was discontinued.

The incidence of neutropenia in patients treated with rifabutin was significantly greater than in patients treated with placebo. Although thrombocytopenia was not significantly more common among rifabutin-treated patients, in rare cases rifabutin has been clearly linked to thrombocytopenia. One patient developed thrombotic thrombocytopenic purpura, which was attributed to rifabutin.

Both rifampin and rifabutin are FDA approved drugs for treatment of tuberculosis. In view of the high dosages required to suppress *M. tuberculosis* and in view of the severe a and numerous adverse reactions associated with administration of these drugs, there clearly is a need for new drugs and methods of treatment for tuberculosis.

Rifalazil has been shown to have antibacterial activity against *Mycobacterium tuberculosis, Mycobacterium avium, Chlamydia pneumoniae, H. pylori* and other bacteria. Despite the adverse reactions described in the clinical trials 001–004, the novel method for treatment of tuberculosis with rifalazil administered once or twice-a-week is a method of choice. It effectively lowers CFU in TB patients when administered in well tolerated doses (10 and 25 mg/dose) once or twice-a-week for 4–62 weeks. At these dosages, the adverse reactions are at most mild or not observable.

Both the animal studies and studies on human volunteers suggest that rifalazil has fewer side effects than rifampin, and rifabutin and has higher anti-bacterial activity, especially against *Mycobacterium tuberculosis, Mycobacterium avium, Chlamydia pneumoniae* and *H. pylori*.

III. Administration and Formulation

The drug product is administered systemically or parenterally, i.e. orally, intravenously, by aerosol, by suppositories or in any other acceptable pharmaceutical form.

Rifalazil may be formulated and administered as standalone drug with various pharmaceutically acceptable additives and excipients, or in combination with other drugs such isoniazid, ethambutol, streptomycin, pyrazinamide, capreomycin, ethionamide, cycloserine, kanamycin, tobramycin or amikacin, with other rifamycins, that is, it can be also combined with rifampin or rifabutin, with other antibacterial agents, analgesics, antitussives, etc. Various ratios of these drugs to each other will depend on the intended use, on the patients symptoms and severity of the disease. Various combinations and ratios of drugs to each other are within the skills of the pharmacist formulating the rifalazil or rifalazil combination with other drugs.

Typically, the drug product will contain rifalazil, mannitol, USP; hydroxypropyl cellulose, NF; colloidal silicon, dioxide, NF; magnesium stearate, NF; polysorbate 80, NF; and water in proportions that permit material flow in capsule-filling equipment. For example, rifalazil will be prepared in No. 3 hard gelatin dark blue opaque snap fit capsules, or as tablets, injectables, suppositories, etc.

For clinical studies described above, rifalazil capsules have been prepared at several different strengths; 5 mg, 25 mg, 50 mg, and 100 mg. The drug in the 5 mg and 50 mg strength capsules has been blended with additional mannitol (placebo) so that the capsules were equivalent in weight and therefore indistinguishable from the 100 mg and placebo capsules, appropriately packaged and labeled. The drug was stored at room temperature.

EXAMPLE 1

Clinical Study Design—Healthy Volunteers

This example describes a design used for clinical studies described above. This design is a typical one. Dosages and drug administration regimen was changed according to the aim of the study.

Study Design

Subjects in an open-label trial received a single or multiple dose of 5, 25, 50 or 300 mg dose of rifalazil. The study was a randomized, double-blind, placebo-controlled intermittent dose study designed to determine a maximum safe dosing regimen.

The subject population was divided into two treatment groups, each consisting of six subjects. Subjects in each group were randomized to receive either placebo or rifalazil once weekly for 4 weeks with a two-week follow-up period. The two treatment groups were separated by at least two weeks to at allow sufficient time to review the safety data. Subjects in all groups received drug or placebo within 30 minutes of eating a standard 60% fat breakfast.

Subjects in Treatment Group 1 were randomized to receive either a 25 mg dose (n=6), a 50 mg dose (n=6), or placebo (n=6) once a week (q.w.) for a total for four weeks.

Randomization and Blinding

Subjects were randomly assigned to and within a treatment group. All studies were blind or double blind.

Patient Selection

The study was conducted with healthy adult volunteers recruited from the population at large.

Dose Selection

Dose selection for this study was based on the safety profile of rifalazil obtained from three previous safety and pharmacokinetic (PK) studies. The results of these studies indicated that the incidence of adverse reactions was greater following daily dosing than after a single dose and that the adverse reactions were more prolonged following daily dosing. Furthermore, there appeared to be a dose-dependent trend in the incidence of adverse reactions. A single 300 mg dose did produce more adverse reactions than either the 30 mg or 100 mg single dose. Similarly, approximately twice as many adverse reactions were recorded for the 25 mg daily dose group (003 trial) than for the 5 mg daily dose group and the adverse reactions were more prolonged than following a single dose.

Drug Formulation

Rifalazil and matching placebo were prepared in No.3 hard gelatin dark blue opaque snap-fit capsules. Rifalazil capsules have been prepared at four different strengths 5 mg, 25 mg, 50 mg and 100 mg. Rifalazil in the 5 mg, 25 mg and 50 mg strength capsules has been blended with additional mannitol (placebo) so that the capsules were equivalent in weight and therefore indistinguishable from the placebo.

Dosage and Administration

All capsules were administered orally with water. Compliance was assessed by visual examination of dosing and of the oral cavity following administration.

EXAMPLE 2

Clinical Study Design for tuberculosis Patients

This example describes design used for clinical studies performed on tuberculosis patients.

The overall clinical studies and conditions were similar to those described in Example 1. Due to ethical considerations, there were no placebo (control) patients in this study. All patients were treated either with 400 mg isoniazid daily, which is a typical and FDA approved TB treatment, or with 400 mg isoniazid in combination with 600 mg rifampin daily, which is also typical and FDA approved TB treatment, or with 400 mg isoniazid daily and 10 mg of rifalazil once-a-week, or with 400 isoniazid daily and 25 mg of rifalazil once-a-week. Both latest regimens were experimental and performed under IND permit from FDA.

Results of the clinical trial 005 on tuberculosis patients are described above in Section II.B.

What is claimed:

1. A method for treatment of bacterial infections caused by *Mycobacterium tuberculosis, Mycobacterium avium* complex, *Chlamydia pneumoniae* or *Helicobacter pylori* in human subjects by once-a-week or twice-a-week administration of rifalazil in a dosage from about 1 to about 100 mg.

2. The method of claim 1 wherein the dosage of rifalazil is from 5 to 50 mg administered once-a-week or twice-a-week.

3. The method of claim 2 wherein the dosage of rifalazil is from 10 to 25 mg administered once-a-week or twice-a-week.

4. The method of claim 3 wherein the bacterial infection is caused by *Mycobacterium tuberculosis*.

5. The method of claim 4 wherein the infection is tuberculosis.

6. The method of claim 5 wherein the tuberculosis is treated by once-a-week or twice-a-week administration of rifalazil for 4 to 62 weeks.

7. The method of claim 6 wherein rifalazil is administered in combination with isoniazid, ethambutol, pyrazinamide, streptomycin, capreomycin, ethionamide, cycloserine, kanamycin, tobramycin or amikacin.

8. The method of claim 7 wherein the tuberculosis is treated for 8 weeks.

9. The method of claim 7 wherein the tuberculosis is treated for 16–26 weeks.

10. The method of claim 1 wherein the infection is caused by *Chlamydia pneumoniae*.

11. The method of claim 10 wherein the *Chlamydia pneumoniae* infection is treated with once-a-week or twice-a-week dose of rifalazil in dose from 1 to about 50 mg orally.

12. The method of claim 1 wherein the infection is caused by *Mycobacterium avium* complex.

13. The method of claim 12 wherein the *Mycobacterium avium* complex infection is treated with once-a-week or twice-a-week dose of 1–50 mg of rifalazil alone or in combination with azithromycin or clanthromycin.

14. The method of claim 1 wherein the rifalazil is administered orally, transdermally, parenterally, topically or by suppositories.

15. The method of claim 14 wherein the topical administration is inhalation, buccal, or transdermal and wherein the parental administration is intravenous, intraperitoneal, subcutaneous or intramuscular.

16. The method of claim 14 wherein the drug is administered orally in tablets, capsules, powders or as sustained release microcapsules.

* * * * *